United States Patent
Wang et al.

(10) Patent No.: US 8,252,808 B2
(45) Date of Patent: Aug. 28, 2012

(54) PROCESS AND COMPOUNDS FOR THE PRODUCTION OF (+)OPIATES

(75) Inventors: Peter X. Wang, Clarkson Valley, MO (US); Tao Jiang, St. Louis, MO (US); Gary L. Cantrell, Troy, IL (US); David W. Berberich, St. Peters, MO (US); Bobby N. Trawick, Florissant, MO (US); Todd Osiek, Ballwin, MO (US); Subo Liao, Ballwin, MO (US); Frank W. Moser, Arnold, MO (US); Joseph P. McClurg, Manchester, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 725 days.

(21) Appl. No.: 12/316,862

(22) Filed: Dec. 17, 2008

(65) Prior Publication Data

US 2009/0156818 A1    Jun. 18, 2009

Related U.S. Application Data

(60) Provisional application No. 61/014,094, filed on Dec. 17, 2007.

(51) Int. Cl.
 *C07D 221/28* (2006.01)
 *A61K 31/4748* (2006.01)

(52) U.S. Cl. .......................... 514/289; 546/74

(58) Field of Classification Search ........... None
See application file for complete search history.

(56) References Cited

U.S. PATENT DOCUMENTS

| | | | |
|---|---|---|---|
| 3,438,989 A | 4/1969 | Shavel, Jr. et al. | |
| 4,368,326 A | 1/1983 | Rice | |
| 5,668,285 A | 9/1997 | Rice et al. | |
| 2005/0038250 A1 | 2/2005 | Linders et al. | |
| 2008/0318966 A1 | 12/2008 | Wang et al. | |
| 2011/0015219 A1 * | 1/2011 | Trawick et al. | 514/278 |

FOREIGN PATENT DOCUMENTS

| | | |
|---|---|---|
| EP | 0 158 476 | 10/1985 |
| EP | 0 168 686 | 1/1986 |
| FR | 1 602 610 | 1/1971 |
| FR | 2 189 403 | 1/1974 |
| WO | WO 99/42105 | 8/1999 |
| WO | WO 2007070703 A2 * | 6/2007 |
| WO | WO 2008/036172 | 3/2008 |

OTHER PUBLICATIONS

Grant & Hackh's Chemical Dictionary (5th Ed. 1987), p. 148.*
Hitotsuyanagi et al., "Synthesis of an antitumor alkaloid sinocculine from sinomenine", Journal of the Chemical Society, Chemical Communications, 23, 1994, pp. 2707-2708, XP 009113662.
Hitotsuyanagi et al., "Syntheses of Antitumor Morphinane Alkaloids, Sinococuline and 6-epi-, 7-epi-, and 6-epi-7-sip-Sinococuline, from Sinomenine", Journal of Organic chemistry, 60(14), 1995, pp. 4549-4558, XP 002919264.
Hong et al., "Preparation of Opium Alkaloids by Palladium Catalyzed Bis-Cyclizations. Formal Total Synthesis of Morphine", Tetrahedron Letters, 35(21), 1994, pp. 3453-3456, XP 002376506.

* cited by examiner

*Primary Examiner* — Michael Barker

(57) ABSTRACT

The invention generally provides processes and intermediate compounds useful for the production of (+)-opiates. Non-limiting examples of (+) opiates that may be derived from one or more compounds of the invention include (+)-noroxymorphone, (+)-naltrexone, (+)-naloxone, (+)-N-cyclopropylmethylnorhydrocodone, (+)-N-cycloproylmethylnorhydromorphone, (+)-N-allylnorhydrocodone, (+)-N-allylnorhydromorphone, (+)-noroxycodone, (+)-naltrexol, (+)-naloxol, and (+)-3-O-methyl-naltrexone.

9 Claims, No Drawings

PROCESS AND COMPOUNDS FOR THE PRODUCTION OF (+)OPIATES

CROSS-REFERENCE TO RELATED APPLICATION

This application claims priority from Provisional Application Ser. No. 61/014,094 filed on Dec. 17, 2007, which is hereby incorporated by reference in its entirety.

FIELD OF THE INVENTION

The present invention generally relates to processes and intermediate compounds useful for the production of (+)-opiates.

BACKGROUND OF THE INVENTION

Morphine and other natural opiates have been used for decades as pain relievers. It is well known, however, that the natural opiates have undesirable side effects and may be habit forming. Recently, unnatural opiates, or the (+) opiate enantiomers, have been shown to have important bioactivities that frequently differ from their (−) counterparts. In order to explore the possible benefits of these compounds, there is a need in the art for processes to prepare (+) opiate compounds.

SUMMARY OF THE INVENTION

One aspect of the invention encompasses a compound comprising formula (I):

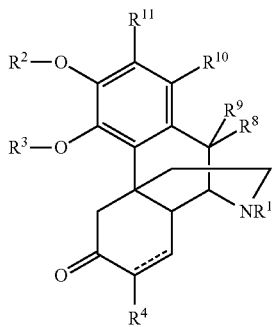

(I)

wherein:
  $R^1$ is selected from the group consisting of hydrogen, and {—}$OCOR^5$;
  $R^2$ is selected from the group consisting of hydrogen, hydrocarbyl, and substituted hydrocarbyl;
  $R^3$ is selected from the group consisting of hydrogen, {—}$OCOR^6$, {—}$OCR^6$, and a bond that forms part of an ether-containing ring, provided, however, if $R^3$ is a bond forming an ether-containing ring then compound (I) is the (+) enantiomer;
  $R^4$ is selected from the group consisting of {—}$OR^7$ and hydrogen;
  $R^5$ and $R^6$ are independently selected from the group consisting of hydrocarbyl and substituted hydrocarbyl;
  $R^7$ is selected from the group consisting of hydrogen, hydrocarbyl, and substituted hydrocarbyl;
  $R^8$ and $R^9$ are independently selected from the group consisting of hydrogen, hydroxy, hydrocarbyl, and substituted hydrocarbyl, or $R^8$ and $R^9$ together form a carbonyl group;
  $R^{10}$ and $R^{11}$ are independently selected from the group consisting of hydrogen, hydrocarbyl, substituted hydrocarbyl, and a halogen; and
  ---- is a single bond or a double bond.

Another aspect of the invention provides a process for the preparation of compound (Ib) according to the following reaction scheme:

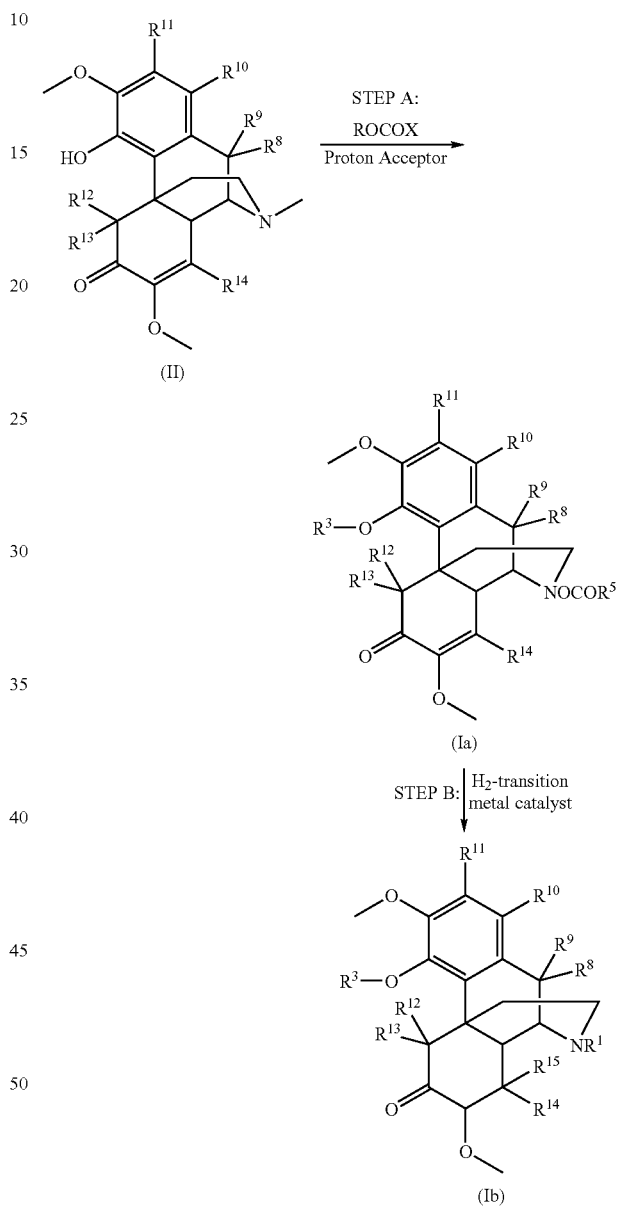

wherein:
  R is selected from hydrocarbyl, and substituted hydrocarbyl;
  $R^1$ is selected from the group consisting of hydrogen and {—}$OCOR^5$;
  $R^3$ is selected from the group consisting of hydrogen, {—}$OCOR^6$, and {—}$OCR^6$;
  $R^5$ and $R^6$ are independently selected from the group consisting of hydrocarbyl and substituted hydrocarbyl;

$R^8$ and $R^9$ are independently selected from the group consisting of hydrogen, hydroxyl, hydrocarbyl, and substituted hydrocarbyl, or $R^8$ and $R^9$ together form a carbonyl group;

$R^{12}$, and $R^{13}$ are independently selected from the group consisting of hydrogen, hydrocarbyl, and substituted hydrocarbyl, or $R^{12}$ and $R^{13}$ together form a carbonyl group;

$R^{10}$, $R^{11}$, and $R^{14}$ are independently selected from the group consisting of hydrogen, hydrocarbyl, substituted hydrocarbyl, and a halogen;

$R^{15}$ is hydrogen; and

X is a halogen.

An additional iteration of the invention provides a process for the preparation of compound (Ib) according to the following reaction scheme:

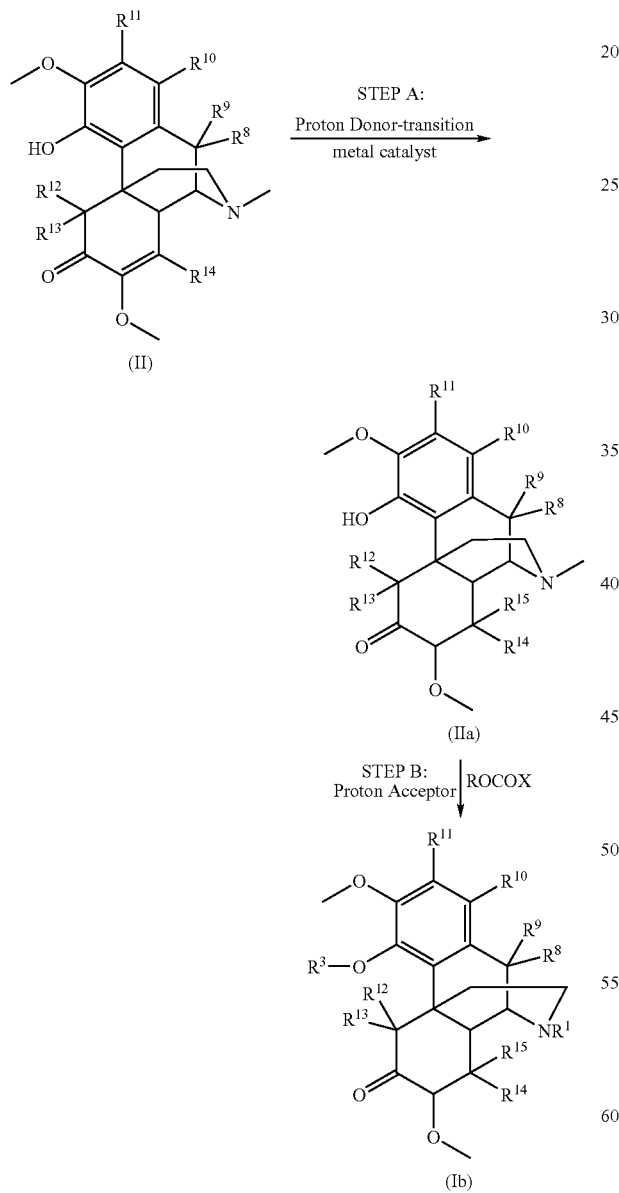

wherein:
R is selected from hydrocarbyl, and substituted hydrocarbyl;

$R^1$ is selected from the group consisting of hydrogen and {—}OCOR$^5$;

$R^3$ is selected from the group consisting of hydrogen, {—}OCOR$^6$, and {—}OCR$^6$;

$R^5$ and $R^6$ are independently selected from the group consisting of hydrocarbyl and substituted hydrocarbyl;

$R^8$ and $R^9$ are independently selected from the group consisting of hydrogen, hydroxyl, hydrocarbyl, and substituted hydrocarbyl, or $R^8$ and $R^9$ together form a carbonyl group;

$R^{12}$, and $R^{13}$ are independently selected from the group consisting of hydrogen, hydrocarbyl, and substituted hydrocarbyl, or $R^{12}$ and $R^{13}$ together form a carbonyl group;

$R^{10}$, $R^{11}$, and $R^{14}$ are independently selected from the group consisting of hydrogen, hydrocarbyl, substituted hydrocarbyl, and a halogen;

$R^{15}$ is hydrogen; and

X is a halogen.

Other aspects and iterations of the invention are described in more detail below.

DETAILED DESCRIPTION OF THE INVENTION

The present invention provides processes and compounds for producing (+) opiates. In particular, the compounds of the present invention may be used as intermediates in the preparation of (+) opiates.

I. Compounds of the Invention

One aspect of the present invention encompasses compounds that may be used as intermediates in the preparation of (+) opiates. For instance, the invention provides a compound comprising formula (I):

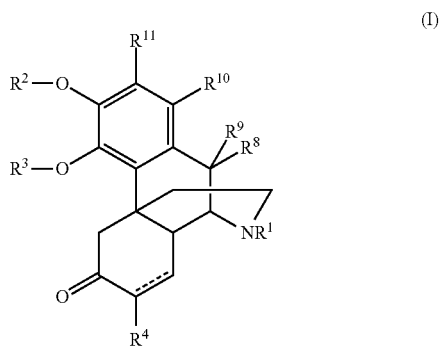

wherein:
$R^1$ is selected from the group consisting of hydrogen, and {—}OCOR$^5$;

$R^2$ is selected from the group consisting of hydrogen, hydrocarbyl, and substituted hydrocarbyl;

$R^3$ is selected from the group consisting of hydrogen, {—}OCOR$^6$, {—}OCR$^6$, and a bond that forms part of an ether-containing ring, provided, however, if $R^3$ is a bond forming an ether-containing ring then compound (I) is the (+) enantiomer;

$R^4$ is selected from the group consisting of {—}OR$^7$ and hydrogen;

$R^5$ and $R^6$ are independently selected from the group consisting of hydrocarbyl and substituted hydrocarbyl;

R[7] is selected from the group consisting of hydrogen, hydrocarbyl, and substituted hydrocarbyl;

R[8] and R[9] are independently selected from the group consisting of hydrogen, hydroxyl, hydrocarbyl, and substituted hydrocarbyl, or R[8] and R[9] together form a carbonyl group;

R[10] and R[11] are independently selected from the group consisting of hydrogen, hydrocarbyl, substituted hydrocarbyl, and a halogen; and ---- is a single bond or a double bond.

In one embodiment for compounds having formula (I), R[5] and R[6] are independently selected from the group comprising an alkyl group having from 1 to 8 carbon atoms, an aryl group, CH$_3$CHCl—{—}, CH$_2$=CH—{—}, and an {—}CH$_2$-aryl group. In a further embodiment, the aryl group may be benzene or substituted benzene.

The compounds described herein may have a (−) or (+) stereochemistry configuration, with respect to the rotation of polarized light. More specifically, each chiral center may have an R or an S configuration. For ease of discussion, the ring atoms of the core morphinan structure referenced herein are numbered as follows:

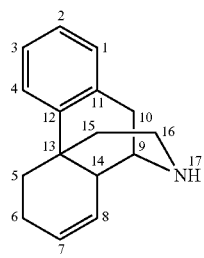

Carbons 13, 14, and 9 are chiral centers. Accordingly, the configuration of a compound of the invention having structure (I), as detailed above, or (Ia), (Ib), or (Ic) as detailed below, may be RRR, RRS, RSR, RSS, SRR, SRS, SSR, or SSS with respect to C(13), C(14), and C(9), provided that the C15 and the C16 atoms are both either on the alpha face of the molecule or the beta face of the molecule. In this context, in some embodiments, the stereochemistry of the C(13), C(14), and C(9) carbons can and will vary without departing from the scope of the invention. For instance, the stereochemistry may be a combination listed in Table A, provided that the C15 and the C16 atoms are both either on the alpha face of the molecule or the beta face of the molecule. In certain embodiments, the compounds of formula (I), (Ia), or (Ib) may be (+) or (−) enantiomers.

TABLE A

| Combination | C13 | C14 | C9 |
|---|---|---|---|
| 1 | R | R | R |
| 2 | R | S | R |
| 3 | R | R | S |
| 4 | R | S | S |
| 5 | S | R | R |
| 6 | S | S | R |
| 7 | S | R | S |
| 8 | S | S | S |

The present invention also encompasses compounds comprising formula (Ia):

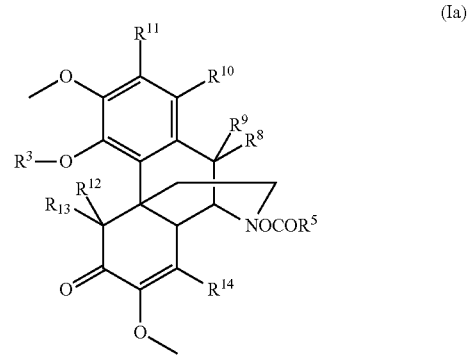

wherein:

R[3] is selected from the group consisting of hydrogen, {—}OCOR[6], and {—}OCR[6]; and R[5] and R[6] are independently selected from the group consisting of hydrocarbyl and substituted hydrocarbyl; and R[8] and R[9] are independently selected from the group consisting of hydrogen, hydroxyl, hydrocarbyl, and substituted hydrocarbyl, or R[8] and R[9] together form a carbonyl group;

R[12] and R[13] are independently selected from the group consisting of hydrogen, hydrocarbyl, and substituted hydrocarbyl, or R[12] and R[13] together form a carbonyl group;

R[10], R[11], and R[14] are independently selected from the group consisting of hydrogen, hydrocarbyl, substituted hydrocarbyl, and a halogen.

In one embodiment for compounds having formula (Ia), R[3] is {—}OCOR[6]; and R[5] and R[6] are independently selected from the group comprising an alkyl group having from 1 to 8 carbon atoms, an aryl group, CH$_3$CHCl—{—}, CH$_2$=CH—{—}, and an {—}CH$_2$-aryl group. In a further embodiment, the aryl group may be benzene or substituted benzene.

In another embodiment for compounds having formula (Ia), R[3] is {—}OCR[6]; and R[5] and R[6] are independently selected from the group consisting of an alkyl group having from 1 to 8 carbon atoms, an aryl group, and {—}CH$_2$-aryl group. In a further embodiment, the aryl group may be benzene or substituted benzene.

In yet another embodiment for compounds having formula (Ia), R[3] is hydrogen; and R[5] is selected from the group consisting of an alkyl group having from 1 to 8 carbon atoms, an aryl group, and an {—}CH$_2$-aryl group. In a further embodiment, the aryl group may be benzene or substituted benzene.

In still another embodiment for compounds having formula (Ia), R[8], R[9], R[10], R[11], R[12], R[13], and R[14] are hydrogen.

In some embodiments for a compound having formula (Ia), the stereochemistry of the C13, C14, and C9 carbons can and will vary without departing from the scope of the invention. For instance, the stereochemistry may be a combination listed in Table A. In certain embodiments, a compound of formula (Ia) may be a (+) or (−) enantiomer.

Additionally, the present invention encompasses compounds comprising formula (Ib):

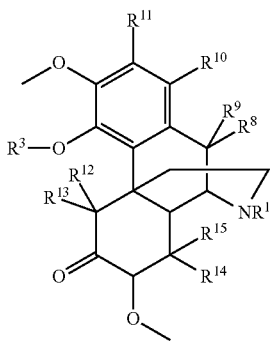

(Ib)

wherein:
R¹ is selected from the group consisting of hydrogen, and {—}OCOR⁵;
R³ is selected from the group consisting of hydrogen, {—}OCOR⁶, and {—}OCR⁶; and
R⁵ and R⁶ are independently selected from the group consisting of hydrocarbyl and substituted hydrocarbyl; and
R⁸ and R⁹ are independently selected from the group consisting of hydrogen, hydroxyl, hydrocarbyl, and substituted hydrocarbyl, or R⁸ and R⁹ together form a carbonyl group;
R¹², and R¹³ are independently selected from the group consisting of hydrogen, hydrocarbyl, and substituted hydrocarbyl, or R¹² and R¹³ together form a carbonyl group;
R¹⁰, R¹¹, R¹⁴ and R¹⁵ are independently selected from the group consisting of hydrogen, hydrocarbyl, substituted hydrocarbyl, and a halogen, or R¹⁴ and R¹⁵ together form a carbonyl group.

In one embodiment for compounds having formula (Ib), R¹ is hydrogen; R³ is {—}OCOR⁶; and R⁶ is independently selected from the group consisting of an alkyl group having from 1 to 8 carbon atoms, an aryl group, CH₃CHCl—{—}, CH₂═CH—{—}, and an {—}CH₂-aryl group. In a further embodiment, the aryl group may benzene or substituted benzene.

In another embodiment for compounds having formula (Ib), R¹ is hydrogen; R³ is {—}OCR⁶; and R⁶ is independently selected from the group consisting of an alkyl group having from 1 to 8 carbon atoms, an aryl group, and an {—}CH₂-aryl group. In a further embodiment, the aryl group may be benzene or substituted benzene.

In yet another embodiment for compounds having formula (Ib), R¹ is {—}OCOR⁵; R³ is {—}OCOR⁶; and R⁵ and R⁶ are independently selected from the group consisting of an alkyl group having from 1 to 8 carbon atoms, an aryl group, and an {—}CH₂-aryl group. In a further embodiment, the aryl group may be benzene or substituted benzene.

In still another embodiment for compounds having formula (Ib), R¹ is {—}OCR⁵; R³ is {—}OCOR⁶; and R⁵ and R⁶ are independently selected from the group consisting of an alkyl group having from 1 to 8 carbon atoms, an aryl group, and an {—}CH₂-aryl group. In a further embodiment, the aryl group may be benzene or substituted benzene.

In another embodiment for compounds having formula (Ib), R¹ and R³ are hydrogen.

In still another embodiment for compounds having formula (Ib), R⁸, R⁹, R¹⁰, R¹¹, R¹², R¹³, R¹⁴ and R¹⁵ are hydrogen.

In some embodiments for a compound having formula (Ib), the stereochemistry of the C13, C14, and C9 carbons can and will vary without departing from the scope of the invention. For instance, the stereochemistry may be a combination listed in Table A, provided that the C15 and the C16 atoms are both either on the alpha face of the molecule or the beta face of the molecule. In certain embodiments, a compound of formula (Ib) may be a (+) or (−) enantiomer.

The present invention further encompasses compounds comprising the (+) enantiomer of formula (Ic):

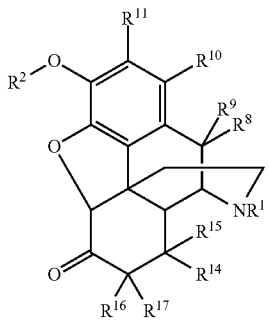

(Ic)

wherein:
R¹ is selected from the group consisting of hydrogen, and {—}OCOR⁵;
R² is selected from the group consisting of hydrogen, and methyl; and
R⁵ is selected from the group consisting of hydrocarbyl and substituted hydrocarbyl; and
R⁸ and R⁹ are independently selected from the group consisting of hydrogen, hydroxyl, hydrocarbyl, substituted hydrocarbyl, or R⁸ and R⁹ together form a carbonyl group;
R¹⁶ and R¹⁷ are independently selected from the group consisting of hydrogen, hydrocarbyl, substituted hydrocarbyl, or R¹⁶ and R¹⁷ together form a carbonyl group; and
R¹⁰, R¹¹, R¹⁴ and R¹⁵ are independently selected from the group consisting of hydrogen, hydrocarbyl, substituted hydrocarbyl, and a halogen, or R¹⁴ and R¹⁵ together form a carbonyl group.

In one embodiment for compounds having formula (Ic), R¹ and R² are hydrogen; and R⁵ is selected from the group consisting of an alkyl group having from 1 to 8 carbon atoms, an aryl group, CH₃CHCl—{—}, CH₂═CH—{—}, and an {—}CH₂-aryl group. In a further embodiment, the aryl group may be benzene or substituted benzene.

In another embodiment for compounds having formula (Ic), R¹ is hydrogen; R² is methyl; and R⁵ is selected from the group consisting of an alkyl group having from 1 to 8 carbon atoms, an aryl group, and an {—}CH₂-aryl group. In a further embodiment, the aryl group may be benzene or substituted benzene.

In yet another embodiment for compounds having formula (Ic), R¹ is {—}OCOR⁵; R² is methyl; and R⁵ is selected from the group consisting of an alkyl group having from 1 to 8 carbon atoms, an aryl group, and an {—}CH₂-aryl group. In a further embodiment, the aryl group may be benzene or substituted benzene.

In still another embodiment for compounds having formula (Ic), R¹ is {—}OCOR⁵; R² is hydrogen; and R⁵ is selected from the group consisting of an alkyl group having from 1 to 8 carbon atoms, an aryl group, and an {—}CH$_2$-aryl group. In a further embodiment, the aryl group may be benzene or substituted benzene.

In another embodiment for compounds having formula (Ic), $R^8$, $R^9$, $R^{10}$, $R^{11}$, $R^{14}$, $R^{15}$, $R^{16}$ and $R^{17}$ are hydrogen.

In some embodiments for a compound having formula (Ic), the stereochemistry of the C(5), C(13), C(14), and C(9) carbons can and will vary without departing from the scope of the invention. For instance, the stereochemistry may be a combination listed in Table B, provided that the C15 and the C16 atoms are both either on the alpha face of the molecule or the beta face of the molecule.

TABLE B

| Combination | C5 | C13 | C14 | C9 |
|---|---|---|---|---|
| 1 | R | R | R | R |
| 2 | R | R | S | R |
| 3 | R | R | R | S |
| 4 | R | R | S | S |
| 5 | R | S | R | R |
| 6 | R | S | S | R |
| 7 | R | S | R | S |
| 8 | R | S | S | S |
| 9 | S | R | R | R |
| 10 | S | R | S | R |
| 11 | S | R | R | S |
| 12 | S | R | S | S |
| 13 | S | S | R | R |
| 14 | S | S | S | R |
| 15 | S | S | R | S |
| 16 | S | S | S | S |

The invention also encompasses salts of any of the above-described compounds having formula (I), (Ia), (Ib), and (Ic). Exemplary salts include without limitation hydrochloride, hydrobromide, phosphate, sulfate, methansulfonate, acetate, formate, tartaric acid, maleic, malic, citrate, isocitrate, succinate, lactate, gluconate, glucuronate, pyruvate, oxalate, fumarate, propionate, aspartate, glutamate, benzoate, methyl fluoride, methyl chloride, methyl bromide, methyl iodide, and the like.

II. Processes for Preparing Compounds of Formula (Ib)

Another aspect of the invention encompasses processes for preparing compounds comprising formula (Ib). In one embodiment, the invention provides a process for preparing a compound comprising formula (Ib) according to Reaction Scheme 1 as shown below. In another embodiment, the invention provides a process for preparing a compound comprising formula (Ib) according to Reaction Scheme 2 as shown below. In each of the above embodiments, the compound comprising formula (Ib) may be used in a process for preparing a compound comprising formula (Ic), as described in further detail in section III below.

(a) Preparation of Compound (Ib) According to Reaction Scheme 1

For purposes of illustration, Reaction Scheme 1 depicts the production of a compound of formula (Ib) from compound (II) in accordance with one aspect of the present invention:

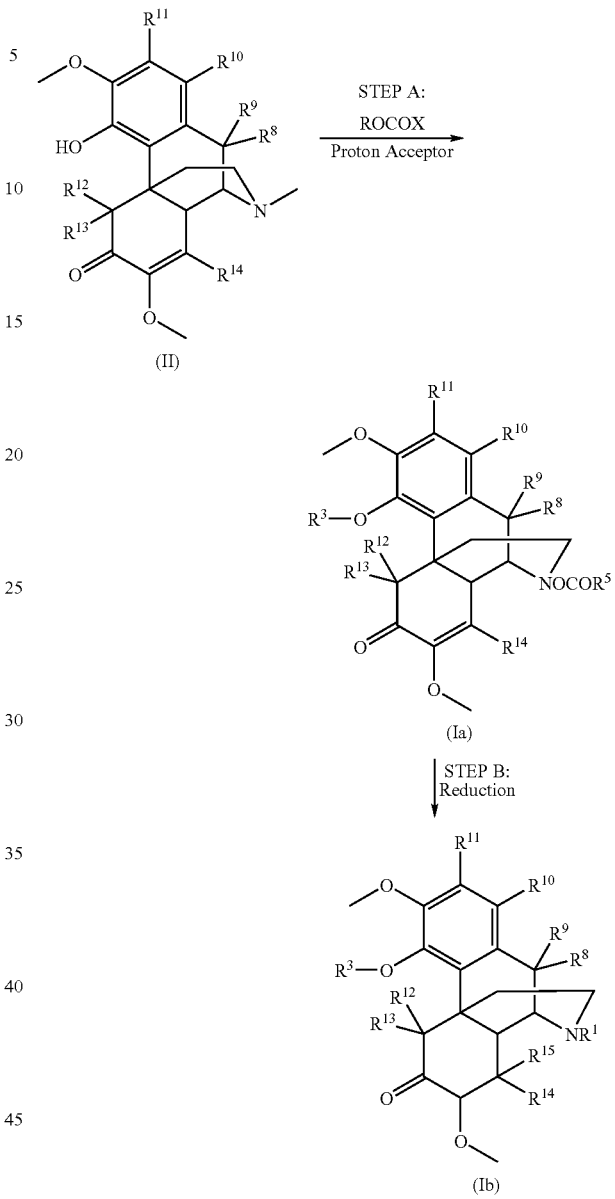

Generally speaking, the process for preparing a compound of formula (Ib) according to Reaction Scheme 1 comprises two steps. In Step A of the process, a compound comprising formula (II) or a salt thereof is contacted with ROCOX, in the presence of a proton acceptor, to form a compound comprising formula (Ia). In Step B of the process, the compound comprising formula (Ia) is reduced to form a compound comprising formula (Ib).

Compounds comprising formula (II) may be prepared using methods known in the art, or, in some embodiments, may be purchased commercially.

i. Preparation of a Compound Comprising Formula (Ia)

In Step A of the process, compound (II) or its salt is contacted with ROCOX, in the presence of a proton acceptor, wherein R is hydrocarbyl or substituted hydrocarbyl, and X is a halogen, to form a compound comprising formula (Ia), wherein:
 R$^3$ is {—}OCR$^6$; and
 R$^5$ and R$^6$ are independently selected from the group consisting of hydrocarbyl and substituted hydrocarbyl; and
 R$^8$ and R$^9$ are independently selected from the group consisting of hydrogen, hydroxyl, hydrocarbyl, and substituted hydrocarbyl, or R$^8$ and R$^9$ together form a carbonyl group;
 R$^{12}$ and R$^{13}$ are independently selected from the group consisting of hydrogen, hydrocarbyl, and substituted hydrocarbyl, or R$^{12}$ and R$^{13}$ together form a carbonyl group;
 R$^{10}$, R$^{11}$, and R$^{14}$ are independently selected from the group consisting of hydrogen, hydrocarbyl, substituted hydrocarbyl, and a halogen.

In one embodiment of Step A, R is selected from the group consisting of an alkyl group having from 1 to 8 carbon atoms, an aryl group, CH$_3$CHCl—{—}, CH$_2$=CH—{—}, and an {—}CH$_2$-aryl group; and X is chlorine.

In some embodiments of Step A, the reaction is conducted in the presence of a solvent. In certain embodiments, the solvent is an aprotic solvent. Non-limiting examples of aprotic solvents include ether solvents, acetone, acetonitrile, benzene, dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethylacetamide (DMAC), N-methylpyrrolidinone (NMP), ethyl acetate, ethyl formate, ethyl-methyl ketone, isobutylmethylketone, n-propylacetate, N-formamide, hexamethylphosphoramide, methyl acetate, N-methylacetamide, N-methylformamide, methylene chloride, nitrobenzene, nitromethane, propionitrile, sulfolane, tetramethylurea, tetrahydrofuran (THF), methyltetrahydrofuran, toluene, chlorobenzene, trichloromethane. In one exemplary embodiment, the aprotic solvent may be selected from the group comprising chloroform, 1,2,-dichloroethane, toluene, ethyl acetate, isopropyl acetate, n-propylacetate, acetonitrile, THF, and methyl butylether.

Generally, the ratio of aprotic solvent to compound (II) may be from about 0.5:1 to about 10:1 (g/g). In some embodiments, the ratio may be from about 1:1, 2:1, 3:1, 4:1, 5:1, 6:1, 7:1, 8:1, 9:1, or 10:1.

The selection of the specific proton acceptor utilized in Step A can and will vary. In general, the proton acceptor has a pKa of between about 7 and about 13, preferably between about 8 and about 10. Representative proton acceptors that may be employed include, but are not limited to, borate salts (such as, for example, NaBO$_3$), di- and tri-basic phosphate salts (such as, for example, Na$_2$HPO$_4$ and Na$_3$PO$_4$), bicarbonate salts (such as, for example, NaHCO$_3$, KHCO$_3$, mixtures thereof, and the like), hydroxide salts (such as, for example, NaOH, KOH, mixtures thereof, and the like), carbonate salts (such as, for example, Na$_2$CO$_3$, K$_2$CO$_3$, mixtures thereof, and the like), organic bases (such as, for example, pyridine, triethylamine, diisopropylethylamine, N-methylmorpholine, N,N-dimethylaminopyridine, and mixtures thereof), organic buffers (such as, for example, N-(2-acetamido)-2-aminoethane sulfonic acid (ACES), N-(2-acetamido)-iminodiacetic acid (ADA), N,N-bis(2-hydroxyethyl)glycine (BICINE), 3-(cyclohexylamino)-1-propanesulfonic acid (CAPS), 2-(cyclohexylamino)ethanesulfonic acid (CHES), 4-(2-hydroxyethyl)-1-piperazinepropanesulfonic acid (EPPS), 4-(2-hydroxyethyl)piperazine-1-ethanesulfonic acid (HEPES), 2-(4-morpholinyl)ethanesulfonic acid (MES), 4-morpholinepropanesulfonic acid (MOPS), 1,4-piperazinediethanesulfonic acid (PIPES), [(2-hydroxy-1,1-bis(hydroxymethyl)ethyl)amino]-1-propanesulfonic acid (TAPS), 2-[(2-hydroxy-1,1-bis(hydroxymethyl)ethyl)amino]ethanesulfonic acid (TES), salts and/or mixtures thereof, and the like), and combinations thereof. Where the proton acceptor is an organic buffer, the organic buffer preferably lacks a hydroxy-substituted nitrogen atom, as this substituent may compete for reaction with the haloformate reactant. In one exemplary embodiment, the proton acceptor may be selected from the group consisting of NaHCO$_3$, KHCO$_3$, LiHCO$_3$, Na$_2$CO$_3$, K$_2$CO$_3$, Li$_2$CO$_3$, and combinations thereof.

As will be appreciated by a skilled artisan, the amount of various reactants used in Step A can and will vary without departing from the scope of the invention. In one embodiment, the molar ratio of compound (II) to ROCOX to proton acceptor is from about 1:3:1 to about 1:12:12. In another embodiment, the molar ratio of compound (II) to ROCOX to proton acceptor is about 1:3:1.

The reaction conditions for Step A, such as reaction time, temperature, and pH may also vary without departing from the scope of the invention. By way of non-limiting example, the pH is generally basic, and the reaction time may range from about 3 hours to about 15 hours. Typically, the reaction is conducted at a temperature ranging from about 45° C. to about 120° C. For instance, the reaction may be conducted at a temperature about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., or about 120° C. In an exemplary embodiment, the reaction is conducted at a temperature ranging from about 45° C. to about 70° C. The reaction is preferably performed under ambient pressure, and preferably in an inert atmosphere (e.g., nitrogen or argon).

A skilled artisan will appreciate that the yield and purity of compound (Ia) can and will vary depending on the reaction conditions used. The yield will generally range from about 70% to about 95%. In some embodiments, the yield may be 70%, 75%, 80%, 85%, 90%, or 95%.

In certain embodiments, the process is conducted in the presence of a water drying reagent such as MgSO$_4$, K$_2$SO$_4$, NaSO$_4$, CaO, and molecular sieves.

In still another embodiment of the process, R$^8$, R$^9$, R$^{10}$, R$^{11}$, R$^{12}$, R$^{13}$, and R$^{14}$ of the compounds having formula (II) or (Ia) are hydrogen.

In some embodiments of the process, the stereochemistry of the C(13), C(14), and C(9) carbons of compound (II) and (Ia) can and will vary without departing from the scope of the invention. For instance, the stereochemistry may be a combination listed in Table A, provided that the C15 and the C16 atoms are both either on the alpha face of the molecule or the beta face of the molecule. In certain embodiments, a compound of formula (II) or (Ia) may be a (+) or (–) enantiomer.

In a further embodiment of Step A, the hydroxyl group on C(4) of compound (II) may be protected. Methods of protecting the C(4) hydroxyl group are known in the art, and may be performed before or after the reaction yielding compound (Ia). In some embodiments, therefore, R$^3$ may be a hydroxyl protecting group, such as {—}OCR$^6$ or {—}OCOR$^6$, wherein R$^6$ may be selected from the group consisting of a hydrocarbyl, or a substituted hydrocarbyl. Other suitable hydroxyl protecting groups include ethers (e.g., allyl, triphenylmethyl (trityl or Tr), benzyl, p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2- trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups for the hydroxy group and the synthesis thereof may be found in "Protective Groups in Organic Synthesis" by T. W. Greene and P. G. M. Wuts, John Wiley & Sons, 1999.

ii. Preparation of a Compound Comprising Formula (Ib)

Step B of the process comprises reducing a compound having formula (Ia) to form a compound comprising formula (Ib):

wherein:

$R^1$ is selected from the group consisting of hydrogen, and {—}OCOR$^5$;

$R^3$ is selected from the group consisting of hydrogen, {—}OCOR$^6$, and {—}OCR$^6$; and $R^5$ and $R^6$ are independently selected from the group consisting of hydrocarbyl and substituted hydrocarbyl; and $R^8$ and $R^9$ are independently selected from the group consisting of hydrogen, hydroxyl, hydrocarbyl, and substituted hydrocarbyl, or $R^8$ and $R^9$ together form a carbonyl group;

$R^{12}$, $R^{13}$ and are independently selected from the group consisting of hydrogen, hydrocarbyl, and substituted hydrocarbyl, or $R^{12}$ and $R^{13}$ together form a carbonyl group;

$R^{10}$, $R^{11}$, $R^{14}$ and $R^{15}$ are independently selected from the group consisting of hydrogen, halogen, hydrocarbyl, and substituted hydrocarbyl, or $R^{14}$ and $R^{15}$ together form a carbonyl group.

In one embodiment of Step B, $R^5$ and $R^6$ are independently selected from the group consisting of an alkyl group having from 1 to 8 carbon atoms, an aryl group, $CH_3CHCl$—{—}, $CH_2$=CH—{—}, and an {—}$CH_2$-aryl group.

A wide variety of reducing approaches may be employed for the reduction reaction in Step B including, for example, chemical reduction, catalytic reduction, and the like. Representative reducing agents for use in catalytic reduction methods with hydrogen include commonly used catalysts such as, for example, platinum catalysts (e.g., platinum black, colloidal platinum, platinum oxide, platinum plate, platinum sponge, platinum wire, and the like), palladium catalysts (e.g., palladium black, palladium on barium carbonate, palladium on barium sulfate, colloidal palladium, palladium on carbon, palladium hydroxide on carbon, palladium oxide, palladium sponge, and the like), nickel catalysts (e.g., nickel oxide, Raney nickel, reduced nickel, and the like), cobalt catalysts (e.g., Raney cobalt, reduced cobalt, and the like), iron catalysts (e.g., Raney iron, reduced iron, Ullmann iron, and the like), and others. In an exemplary embodiment, compound (Ia) is reduced using catalytic reduction (e.g., Pd/C catalyzed transfer hydrogenation). Preferred catalysts include transition metal catalysts selected from the group consisting of Pd/C, Pt/C, Ru/C, and Rh/C.n one embodiment, the molar ratio of compound (Ia) to transition metal catalyst is from about 1:0.0005 to about 1:0.05. In another embodiment, the ratio is from about 1:0.0008 to about 1:0.0015.

In certain embodiments of Step B, the reaction is conducted in the presence of an alcohol-containing solvent. The selection of an alcohol-containing solvent, and the amount utilized, can and will vary without departing from the scope of the invention. For example, suitable alcohols include for example, methanol, ethanol, isopropyl alcohol, isobutyl alcohol, t-butyl alcohol, n-propyl alcohol, n-butyl alcohol, and combinations thereof. In one embodiment, the alcohol containing solvent is a methanol containing solvent. Generally, the ratio of methanol containing solvent to compound (Ia) is from about 0.5:1 to about 2.0:1 (g/g).

The reaction conditions for Step B of the process, such as pressure, temperature, and reaction time may also vary without departing from the scope of the invention. For instance, when a catalyst is used for reduction, the reaction is conducted in the presence of pressurized hydrogen. Typically, the hydrogen pressure may be between about 0 and about 500 PSI. In some embodiments, the hydrogen pressure may be about 20, about 40, about 60, about 80, about 100, about 120, about 140, about 160, about 180, about 200, about 220, about 240, about 260, about 280, about 300, about 320, about 340, about 360, about 380, about 400, about 420, about 440, about 460, about 480, or about 500 PSI. In an exemplary embodiment, the hydrogen pressure may be between about 30 and about 60 PSI.

Additionally, the reaction may be conducted at a temperature ranging from about 20° C. to about 120° C. For instance, the reaction may be conducted at a temperature about 20° C, about 25° C, about 30° C., about 40° C., about 45° C., about 50° C., about 55° C, about 60° C., about 65° C., about 70° C., about 75° C., about 80° C., about 85° C., about 90° C., about 95° C., about 100° C., about 105° C., about 110° C., about 115° C., or about 120° C. In an exemplary embodiment, the reaction is conducted at a temperature ranging from about 45° C. to about 60° C.

A skilled artisan will appreciate that the yield and purity of compound (Ib) can and will vary depending on the reaction conditions used. Generally, the yield of compound (Ib) may be about 70% to about 95%. In some embodiments, the yield is about 70%, 75%, 80%, 85%, 90%, or 95%.

In still another embodiment of the process, $R^8$, $R^9$, $R^{10}$, $R^{11}$, $R^{12}$, $R^{13}$, $R^{14}$ and $R^{15}$ of the compounds having formula (II) or (Ia) may be hydrogen.

In some embodiments of the process, the stereochemistry of the C(13), C(14), and C(9) carbons of compound (Ia) and (Ib) can and will vary without departing from the scope of the invention. For instance, the stereochemistry may be a combination listed in Table A, provided that the C15 and the C16 atoms are both either on the alpha face of the molecule or the beta face of the molecule. In certain embodiments, a compound of formula (Ia) and (Ib) may be a (+) or (−) enantiomer.

In a further embodiment of the process, the oxygen on C(4) of compound (Ia) or (Ib) may be protected. Methods of protecting the C(4) hydroxyl group are known in the art and are described above, and may be performed before or after the reaction yielding compound (Ib). In some embodiments, therefore, $R^3$ may be a hydroxyl protecting group, such as {—}OCR$^6$ or {—}OCOR$^6$ wherein $R^6$ may be selected from the group consisting of hydrocarbyl, or a substituted hydrocarbyl.

In one embodiment, $R^3$ of compound (Ia) is {—}OCOR$^5$, wherein $R^5$ is {—}$CH_2$-aryl. In another embodiment, $R^3$ of compound (Ib) is hydrogen; and $R^1$ is hydrogen.

(b) Preparation of Compound (Ib) According to Reaction Scheme 2

For purposes of illustration, Reaction Scheme 2 depicts the production of compound (Ib) from compound (II) in accordance with one aspect of the present invention:

Reaction Scheme 2

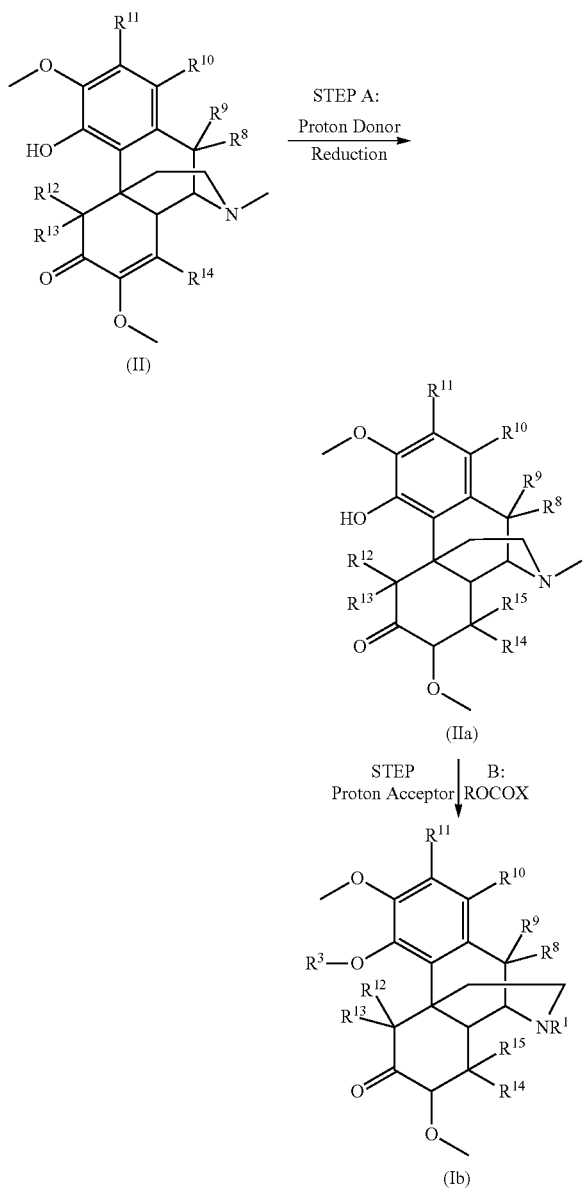

Generally speaking, the process for preparing a compound of formula (Ib) according to Reaction Scheme 2 comprises two steps. Step A of the process comprises reducing compound (II) to form a compound comprising formula (IIa). Step B of the process comprises contacting compound (IIa) with a proton acceptor and ROCOX, wherein R is hydrocarbyl or substituted hydrocarbyl; and X is a halogen, to form a compound of formula (Ib).

i. Preparation of a Compound Comprising Formula (IIa)

In the Step A of Reaction Scheme 2, compound (II) is reduced in the presence of a proton donor to form compound (IIa), wherein $R^8$ and $R^9$ are independently selected from the group consisting of hydrogen, hydroxyl, hydrocarbyl, and substituted hydrocarbyl, or $R^8$ and $R^9$ together form a carbonyl group;

$R^{12}$ and $R^{13}$ are independently selected from the group consisting of hydrogen, hydrocarbyl, and substituted hydrocarbyl, or $R^{12}$ and $R^{13}$ together form a carbonyl group; and $R^{10}$, $R^{11}$, $R^{14}$ and $R^{15}$ are independently selected from the group consisting of hydrogen, hydrocarbyl, substituted hydrocarbyl, and a halogen, or $R^{14}$ and $R^{15}$ together form a carbonyl group.

In Step A, compound (II) may be reduced in accordance with any of the reduction methods described for Step B of Reaction Scheme 1. In an exemplary embodiment, the reduction is conducted with a transition metal catalyst in the presence of proton donor. The selection of a transition metal catalyst and proton donor, and the amount utilized, can and will vary without departing from the scope of the invention. Non-limiting examples of transition metal catalysts may include Pd/C, Pt/C, Ru/C, and Rh/C.

The proton donor generally has a PKa less than about 6. Suitable proton donors having this characteristic include, but are not limited to HOAc, $HCO_2H$, $MeSO_3H$, poly $H_3PO_4$, $H_3PO_4$, $H_2SO_4$, HCl, HBr, HI, $CF_3SO_3H$, and toluenesulfonic acid. Usually, the molar ratio of compound (II) to proton donor to transition metal catalyst is from about 1:0.5:0.0005 to about 1:10:0.05. In some embodiments, the ratio is from about 1:0.5:0.0008 to about 1:2.0:0.015.

In various embodiments of Step A, the reaction is conducted in the presence of an alcohol-containing solvent. Suitable alcohol-containing solvents are as described in Reaction Scheme 1. In some exemplary embodiments, the alcohol-containing solvent is a methanol containing solvent. Advantageously, the product compound (IIa) may be isolated as a solid after the reaction mixture is filtered and basified when the reaction is carried out in a mixture of a methanol containing solvent and water. The selection of a methanol-containing solvent, and the amount utilized, can and will vary without departing from the scope of the invention. In one embodiment, the ratio of methanol containing solvent to compound (II) is from about 0.5:1 to about 2.0:1 (g/g).

The reaction conditions for Step A of the process, such as pressure, temperature, and reaction time may also vary without departing from the scope of the invention. For instance, the hydrogen pressure is between about 0 and about 500 PSI. In one embodiment, the hydrogen pressure may be about 20, about 40, about 60, about 80, about 100, about 120, about 140, about 160, about 180, about 200, about 220, about 240, about 260, about 280, about 300, about 320, about 340, about 360, about 380, about 400, about 420, about 440, about 460, about 480, or about 500 PSI. In an exemplary embodiment, the hydrogen pressure is between about 30 and about 60 PSI.

Additionally, the reaction may be conducted at a temperature ranging from about 20° C. to about 120° C. For instance, the reaction may be conducted at a temperature about 20° C., about 25° C., about 30° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., or about 120° C. In an exemplary embodiment, the reaction is conducted at a temperature ranging from about 45° C. to about 60° C.

A skilled artisan will appreciate that the yield of compound (IIa) can and will vary depending on the reaction conditions used. Generally, the yield of compound (IIa) is from about 90% to about 95%.

In still another embodiment of the process, $R^8$, $R^9$, $R^{10}$, $R^{11}$, $R^{12}$, $R^{13}$, $R^{14}$ and $R^{15}$ of the compounds having formula (II) or (IIa) may be hydrogen.

In some embodiments of the process, the stereochemistry of the C(13), C(14), and C(9) carbons of compound (II) and (IIa) can and will vary without departing from the scope of the invention. For instance, the stereochemistry may be a combination listed in Table A, provided that the C15 and the C16 atoms are both either on the alpha face of the molecule or the beta face of the molecule. In certain embodiments, a compound of formula (II) or (IIa) may be a (+) or (−) enantiomer.

In a further embodiment of the process, the hydroxyl on C(4) of compound (II) or (IIa) may be protected. Methods of protecting the C(4) hydroxyl group are known in the art, and may be performed before or after the reaction yielding compound (IIa). In some embodiments, the hydroxyl protecting group may be {—}$OCR^6$ or {—}$OCOR^6$, wherein $R^6$ may be selected from the group consisting of a hydrocarbyl, or a substituted hydrocarbyl.

ii. Preparation of a Compound Comprising Formula (Ib)

Step B of the process comprises contacting compound (IIa) with a proton acceptor and ROCOX, wherein R is hydrocarbyl or substituted hydrocarbyl; and X is a halogen, to form compound (Ib), wherein:
 $R^1$ is selected from the group consisting of hydrogen, and {—}$OCOR^5$;
 $R^3$ is selected from the group consisting of hydrogen and {—}$OCOR^6$;
 $R^5$ and $R^6$ are independently selected from the group consisting of hydrocarbyl and substituted hydrocarbyl; and
 $R^8$ and $R^9$ are independently selected from the group consisting of hydrogen, hydroxyl, hydrocarbyl, and substituted hydrocarbyl, or $R^8$ and $R^9$ together form a carbonyl group;
 $R^{12}$ and $R^{13}$ are independently selected from the group consisting of hydrogen, hydrocarbyl, and substituted hydrocarbyl, or $R^{12}$ and $R^{13}$ together form a carbonyl group;
 $R^{10}$, $R^{11}$, $R^{14}$, and $R^{15}$ are independently selected from the group consisting of hydrogen, hydrocarbyl, substituted hydrocarbyl, and a halogen, or $R^{14}$ and $R^{15}$ together form a carbonyl group.

In one embodiment of Step B, $R^5$ and $R^6$ are independently selected from the group consisting of an alkyl group having from 1 to 8 carbon atoms, an aryl group, $CH_3CHCl$—{—}, $CH_2$=CH—{—}, and an {—}$CH_2$-aryl group, and X is chlorine.

In some embodiments of Step B, the reaction is conducted in the presence of a solvent. In certain embodiments, the solvent is an aprotic solvent. Suitable aprotic solvents are as described for Reaction Scheme 1. Generally, the ratio of aprotic solvent to compound (IIa) may be from about 0:1 to about 10:1 (g/g). In some embodiments, the ratio may be 1:1, 2:1, 3:1, 4:1, 5:1, 6:1, 7:1, 8:1, 9:1, or 10:1.

The selection of the specific proton acceptor utilized can and will vary. Suitable proton acceptors are as described in Reaction Scheme 1.

As will be appreciated by a skilled artisan, the amount of various reactants used in Step B can and will vary without departing from the scope of the invention. In one embodiment, the molar ratio of compound (IIa) to ROCOX to proton acceptor is from about 1:2:1 to about 1:20:20. In another embodiment, the ratio is from about 1:3:3 to about 1:6:6.

The reaction conditions for Step B, such as reaction time, temperature, and pH may also vary without departing from the scope of the invention. By way of non-limiting example, the pH is generally basic, and the reaction time may range from about 3 hours to about 15 hours. Typically, the reaction is conducted at a temperature ranging from about 45° C. to about 120° C. For instance, the reaction may be conducted at a temperature about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., or about 120° C. In an exemplary embodiment, the reaction is conducted at a temperature ranging from about 45° C. to about 70° C. The reaction is preferably performed under ambient pressure, and preferably in an inert atmosphere (e.g., nitrogen or argon).

A skilled artisan will appreciate that the yield and purity of compound (Ib) can and will vary depending on the reaction conditions used. The yield will generally range from about 70% to about 95%. In some embodiments, the yield is about 70%, 75%, 80%, 85%, 90%, or 95%.

In still another embodiment of the process, $R^8$, $R^9$, $R^{10}$, $R^{11}$, $R^{12}$, $R^{13}$, $R^{14}$ and $R^{15}$ of the compounds having formula (IIa) or (Ib) may be hydrogen.

In some embodiments of the process, the stereochemistry of the C(13), C(14), and C(9) carbons of compound (IIa) and (Ib) can and will vary without departing from the scope of the invention. For instance, the stereochemistry may be a combination listed in Table A, provided that the C15 and the C16 atoms are both either on the alpha face of the molecule or the beta face of the molecule. In certain embodiments, a compound of formula (IIa) or (Ib) may be a (+) or (−) enantiomer.

In a further embodiment of the process, the hydroxyl on C(4) of compound (IIa) or (Ib) may be protected. Methods of protecting the C(4) hydroxyl group are known in the art, and may be performed before or after the reaction yielding compound (Ib). In some embodiments, the hydroxyl protecting group may be {—}$OCR^6$ or {—}$OCOR^6$, wherein $R^6$ may be selected from the group consisting of a hydrocarbyl or a substituted hydrocarbyl.

III. Processes for Preparing Compounds of Formula (Ic)

Another aspect of the invention encompasses processes for preparing compounds comprising formula (Ic). In an embodiment, a compound comprising formula (Ic) is prepared from a compound comprising formula (Ib), wherein the compound comprising formula (Ib) was prepared from compound (II) according to Reaction Scheme 1. Alternatively, a compound comprising formula (Ic) is prepared from a compound comprising formula (Ib), wherein the compound comprising formula (Ib) was prepared from compound (II) according to Reaction Scheme 2.

In each of the above embodiments for preparing a compound comprising (Ic), the process comprises contacting a compound comprising formula (Ib) with a proton donor and a scavenger to form a compound comprising formula (Ic),

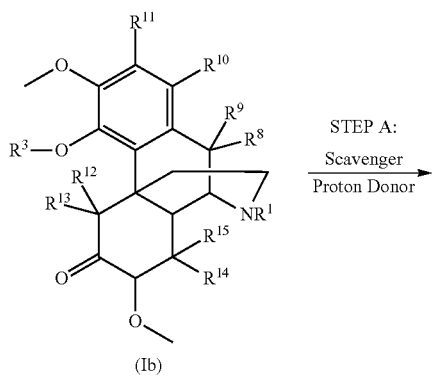

STEP A:
Scavenger
Proton Donor (Ib)

-continued

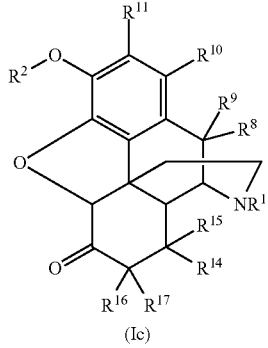

(Ic)

wherein:
R¹ is selected from the group consisting of hydrogen, hydrocarbyl, substituted hydrocarbyl, and {—}OCOR⁵;
R² is selected from the group consisting of hydrogen and hydrocarbyl;
R3 is selected from the group consisting of hydrogen, hydrocarbyl, substituted hydrocarbyl, {—}OCOR⁵, and {—}OCR⁶;
R⁵ and R⁶ are independently selected from the group consisting of hydrocarbyl and substituted hydrocarbyl;
R⁸ and R⁹ are independently selected from the group consisting of hydrogen, hydroxyl, hydrocarbyl, and substituted hydrocarbyl, or R⁸ and R⁹ together form a carbonyl group;
R¹², R¹³, R¹⁶ and R¹⁷ are independently selected from the group consisting of hydrogen, hydrocarbyl, substituted hydrocarbyl, or R¹⁶ and R¹⁷ together form a carbonyl group; and
R¹⁰, R¹¹, R¹⁴, and R¹⁵ are independently selected from the group consisting of hydrogen, hydrocarbyl, substituted hydrocarbyl, and a halogen, or R¹⁴ and R¹⁵ together form a carbonyl group.

In one embodiment of the process, R⁵ and R⁶ are independently selected from the group consisting of an alkyl group having from 1 to 8 carbon atoms, an aryl group, CH₃CHCl—{—}, CH₂=CH—{—}, and an {—}CH₂-aryl group.

The selection of a specific proton acceptor for use in the process can and will vary. Suitable proton acceptors are described in the process for Reaction Schemes 1 and 2.

The choice of alcohol scavenger can and will vary without departing from the scope of the invention. In an exemplary embodiment, the alcohol scavenger is a methanol scavenger. Suitable examples of methanol scavengers may include P₂O₅, POCl₃, POBr₃, PCl₃, PBr₃, SOCl₂, SOBr₂, MeSO₂Cl, (MeSOP₂)₂O, SO₃, (CF₃SO₂)₂O, and (CF₃CO)₂O.

As will be appreciated by a skilled artisan, the amount of various reactants used in process can and will vary without departing from the scope of the invention. In one embodiment, the molar ratio of compound (Ib) to scavenger to proton donor is from about 1:0.5:2 to about 1:2:20. In another embodiment, the ratio is from about 1:1:3 to about 1:1:5.

In some embodiments of the process, the reaction is conducted in the presence of a solvent. In certain embodiments, the solvent is an aprotic solvent. Suitable aprotic solvents are as described above for Reaction Schemes 1 and 2. In one embodiment, the ratio of aprotic solvent to compound (Ib) is from about 0:1 to about 10:1 (g/g). In another embodiment, the ratio is about 1:1, 2:1, 3:1, 4:1, 5:1, 6:1, 7:1, 8:1, 9:1, or 10:1.

The reaction conditions for the process, such as temperature, and pH may also vary without departing from the scope of the invention. By way of non-limiting example, the reaction may be conducted at a temperature ranging from about 0° C. to about 100° C. For instance, the reaction may be conducted at a temperature about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C. In an exemplary embodiment, the reaction may be conducted at a temperature ranging from about 25° C. to about 70° C. The reaction is preferably performed under ambient pressure, and preferably in an inert atmosphere (e.g., nitrogen or argon).

A skilled artisan will appreciate that the yield and purity of compound (Ic) can and will vary depending on the reaction conditions used. The yield will generally range from about 20% to about 80%. In some embodiments, the yield may be about 20%, 25%, 30%, 35%, 40%, 45%, 50%, 55%, 60%, 65%, 70%, 75%, or 80%.

In still another embodiment of the process, R⁸, R⁹, R¹⁰, R¹¹, R¹², R¹³, R¹⁴, R¹⁵, R¹⁶ and R¹⁷ of the compounds having formula (Ib) or (Ic) may be hydrogen.

In some embodiments of the process, the stereochemistry of the C(13), C(14), and C(9) carbons of compound (Ib) can and will vary without departing from the scope of the invention. For instance, the stereochemistry may be a combination listed in Table A, provided that the C15 and the C16 atoms are both either on the alpha face of the molecule or the beta face of the molecule. In certain embodiments, a compound of formula (Ib) may be a (+) or (−) enantiomer. Additionally, the stereochemistry of the C(5), C(13), C(14), and C(9) carbons of compound (Ic) can and will vary without departing from the scope of the invention. For instance, the stereochemistry may be a combination listed in Table B, provided that the C15 and the C16 atoms are both either on the alpha face of the molecule or the beta face of the molecule. In certain embodiments, compound (Ic) may be a (+) or a (−) enantiomer.

In a further embodiment of the process, the hydroxyl on C(4) of compound (Ib) may be protected. Methods of protecting the C(4) hydroxyl group are known in the art, and may be performed before the reaction yielding compound (Ic). In some embodiments, the hydroxyl protecting group may be {'}OCR⁶ or {—}OCOR⁶, wherein R⁶ may be selected from the group consisting of a hydrocarbyl or a substituted hydrocarbyl.

IV. Processes for Preparing Compounds from Compound (Ic)

A further aspect of the invention encompasses processes for preparing compounds from compound (Ic) that may be used in further processes to produce one or more (+)-opiates. In one embodiment, (+)-norhydrocodone is prepared from compound (Ic). In another embodiment, (+)-norhydromorphone is prepared from compound (Ic). Both (+)-norhydrocodone and (+)-norhydromorphone, for example, may be used in further processes to produce one or more (+)-opiates. For instance, compounds that are N-substituted with CH₂=CHCH₂—{—} or cyclopropylCH₂—{—} may be produced.

(a) Preparation of (+)-Norhydrocodone from (Ic)

(+)-Norhydrocodone may be prepared by contacting compound (Ic) with a proton donor according to the reaction scheme:

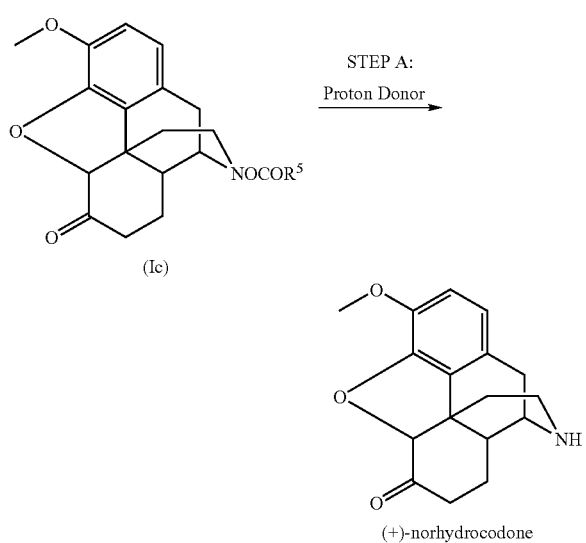

wherein:

R[5] is selected from the group comprising hydrocarbyl, or substituted hydrocarbyl.

The selection of the proton donor can and will vary depending on the reagents and the reaction conditions. Suitable proton donors are as described in Reaction Schemes 1 and 2. In one exemplary embodiment, the proton donor is selected from the group consisting of $MeSO_3H$, poly $H_3PO_4$, $H_3PO_4$, $H_2SO_4$, HCl, HBr, $CF_3SO_3H$, and toluenesulfonic acid.

In some embodiments, the reaction is conducted in the presence of a protic solvent. For instance, the protic solvent may be selected from the group consisting of water, an alcohol having from 1 to 8 carbon atoms, and an organic solvent having the formula $R^aCO_2H$, wherein $R^a$ is hydrocarbyl. Generally speaking, the ratio of protic solvent to compound (Ic) may be from about 1:1 to about 5:1 (g/g). In one embodiment, the ratio is about 2:1 to about 3:1 (g/g).

A skilled artisan will appreciate that the ratio of compound (Ic) to proton donor for preparing (+) norhydrocodone can and will vary without departing from the scope of the invention. Typically, the molar ratio of compound (Ic) to proton donor is from about 1:2 to about 1:10. In some embodiments, the ratio is about 1:2, 1:3, 1:4, 1:5, 1:6, 1:7, 1:8, 1:9, or 1:10.

The reaction conditions for the process may also vary without departing from the scope of the invention. By way of non-limiting example, the reaction may be conducted at a temperature ranging from about 80° C. to about 150° C. For instance, the reaction may be conducted at a temperature of about 80° C., about 85° C., about 90° c, about 95° C., about 100° C., about 105° C., about 110° C., about 115° C., about 120° C., about 125° C., 130° C., about 135° C., about 140° C., about 145° C., or about 150° C. In an exemplary embodiment, the reaction is conducted at a temperature ranging from about 95° C. to about 110° C. The reaction is preferably performed under ambient pressure, and preferably in an inert atmosphere (e.g., nitrogen or argon).

A skilled artisan will appreciate that the yield and purity of (+)-norhydrocodone produced from compound (Ic) can and will vary depending on the reaction conditions used. The yield will generally range from about 70% to about 95%. In some embodiments, the yield may be about 70%, 75%, 80%, 85%, 90%, or 95%.

In another embodiment, (+)-norhydrocodone may be prepared from a compound comprising formula (Ib) by sequentially treating the (Ib) compound with an alcohol scavenger and a proton donor, as described above to prepare a compound comprising formula (Ic), and then treating compound (Ic) with a proton donor to form (+)-norhydrocodone. Such sequential reactions may be performed in the same reaction vessel. For instance, in one embodiment, treatment of O—R[5]OCO—N—R[5]OCO-7,8-dihydronorsinomenine with a methanol scavenger, such as $POCl_3$ in the presence of a proton donor, such as $MeSO_3H$, forms the (Ic) compound N—R[5]OCO-norhydrocodone. Addition of a proper amount of protic solvent such as water and propionic acid to the reaction mixture, followed by heating at 100° C. will form (+)-norhydrocodone.

In some embodiments of the process, the stereochemistry of C(5), C(13), C(14), and C(9) carbons of compound (Ic) or (+)-norhydrocodone can and will vary without departing from the scope of the invention. For instance, the stereochemistry may be a combination listed in Table B, provided that the C15 and the C16 atoms are both either on the alpha face of the molecule or the beta face of the molecule.

(b) Preparation of (+)-Norhydromorphone (+)-Norhydromorphone may be prepared from (+)-norhydrocodone. Typically, the process comprises contacting (+)-norhydrocodone with an O-demethylation reagent according to the reaction scheme:

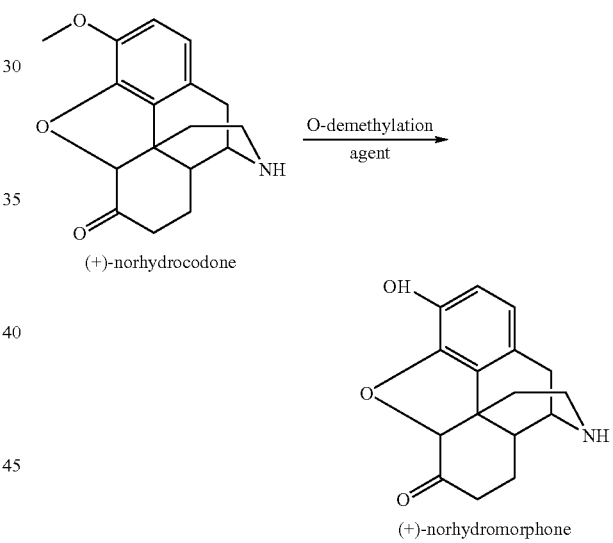

The selection and amount of the O-demethylation agent can and will vary depending on the reaction conditions. In one embodiment, the O-demethylation reagent is selected from the group consisting of HBr, $BBr_3$, and methionine/$MeSO_3H$. In some embodiments, the molar ratio of (+)-norhydrocodone to O-demethylation reagent is from about 1:2 to about 1:6. In other embodiments, the ratio is from about 1:2.5 to about 1:4.

The reaction conditions for the process also can and will vary without departing from the scope of the invention. By way of non-limiting example, in one embodiment the reaction is conducted at a temperature ranging from about 0° C. to about 150° C. In another embodiment, the reaction is conducted at a temperature ranging from about 0° C. to about 30° C. when the O-demethylation reagent is $BBr_3$, or from about 90° C. to about 120° C. when the O-demethylation reagent is HBr or methionine/$MeSO_3H$. The reaction is preferably performed under ambient pressure, and preferably in an inert atmosphere (e.g., nitrogen or argon).

A skilled artisan will appreciate that the yield and purity of (+)-norhydromorphone produced from (+)-norhydrocodone can and will vary depending on the reaction conditions used. The yield will generally range from about 60% to about 80%. In some embodiments, the yield may be about 60%, 65%, 70%, 75%, or 80%.

In another embodiment, (+)-norhydromorphone may be prepared from a compound comprising formula (Ib) by sequentially treating the (Ib) compound with a methanol scavenger and a proton donor, as described above to prepare a compound comprising formula (Ic), then adding a proton donor to form (+)-norhydrocodone, and then adding an O-demethylation agent to form (+) norhydromorphone. Such sequential reactions may be performed in the same reaction vessel. For instance, in one embodiment, treatment of O—$R^5$OCO—N—$R^5$OCO-7,8-dihydronorsinomenine with a methanol scavenger, such as $POCl_3$ in the presence of a proton donor, such as $MeSO_3H$, forms the (Ic) compound N—$R^5$OCO-norhydrocodone. Addition of a proper amount of protic solvent such as water and propionic acid to the reaction mixture, followed by heating at 100° C. will form (+)-norhydrocodone. Addition of methionine to the reaction mixture followed by heating at 100° C. will form (+)-norhydromorphone. In another embodiment, treatment of O—$R^5$OCO—N—$R^5$OCO-7,8-dihydronorsinomenine with a methanol scavenger and O-demethylation agent, such as $BBr_3$ in the presence of an acid, such as HBr, in chloroform forms the (Ic) compound N—$R^5$OCO-norhydrocodone, and then, N—$R_5$OCO-norhydromorphone. Heating in a proton donor solution will form (+)-norhydromorphone.

(c) Preparation of (+)-Opiates

Various (+)-opiates may be derived from one or more compounds of the present invention, including but not limited to compounds (Ic) or either of (+)-norhydrocodone or (+)-norhydromorphone. Non-limiting examples of suitable (+) opiates that may be derived from one or more compounds of the invention include (+)-noroxymorphone, (+)-naltrexone, (+)-naloxone, (+)-N-cyclopropylmethylnorhydrocodone, (+)-N-cycloproylmethylnorhydromorphone, (+)-N-allylnorhydrocodone, (+)-N-allylnorhydromorphone, (+)-noroxycodone, (+)-naltrexol (including both 6-alpha and 6-beta), (+)-naloxol (including both 6-alpha and 6-beta) and (+)-3-O-methyl-naltrexone.

Definitions

The term "acyl," as used herein alone or as part of another group, denotes the moiety formed by removal of the hydroxy group from the group COOH of an organic carboxylic acid, e.g., RC(O)—, wherein R is $R_1$, $R_1O$—, $R_1R_2N$—, or $R_1S$—, $R_1$ is hydrocarbyl, heterosubstituted hydrocarbyl, or heterocyclo, and $R_2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alcohol scavenger" as used herein is a reagent that can react with an alcohol and release an acid at the same time.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkaryl" or "alkylaryl" as used herein describes groups which are preferably aryl groups having a lower alkyl substituent, such as toluyl, ethylphenyl, or methylnapthyl.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aralkyl" as used herein describes groups which are preferably lower alkyl containing from one to eight carbon atoms having an aryl substituent, such as benzyl; phenylethyl, or 2-napthylmethyl.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

The terms "hydroxy protecting group" as used herein denote a group capable of protecting a free hydroxy group ("protected hydroxy"), which, subsequent to the reaction for which protection is employed, may be removed without disturbing the remainder of the molecule.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compounds, products and methods without departing from the scope of the invention, it is intended that all matter contained in the above description and in the examples given below, shall be interpreted as illustrative and not in a limiting sense.

EXAMPLES

The following examples illustrate various iterations of the invention.

Example 1

Preparation of 7,8-Dihydrosinomenine Via Step A of Reaction Scheme 2

Sinomenine.HCl.xH$_2$O was suspended in methanol (1.0 mL per gram of sinomenine) and water (3.0 mL per gram of sinomenine). Acetic acid (HOAc) (0.086 mL per gram of sinomenine) and 5% Pd/C (0.05 g per gram of sinomenine) was added. The mixture was stirred under hydrogen (40 psi) and was heated to 50° C. until the absorption of hydrogen stopped (approximately 4 to 10 hours). The pure product, 7,8-dihydrosinomenine, was obtained as solids in 85%-95% yield after the reaction mixture was neutralized, filtrated, and dried.

Example 2

Preparation of a Compound Comprising Formula (Ib) Via Step B of Reaction Scheme 2

7,8-dihydrosinomenine (3.30 g, 10 mmol) was suspended in CHCl$_3$ (15 mL). NaHCO$_3$ (6 g) and MgSO$_4$ (1.5 g) were added. The mixture was stirred and heated to 64° C. The mixture was reacted with 3 to 4 equivalents of 1-chloroethyl chloroformate (EtOCOCl), added drop-wise, at a temperature of 62° C. to 66° C. Water (50 mL) was added and the mixture was stirred for 30 minutes to dissolve all of the solids. Chloroform (15 mL) was added and the organic layer was separated and stirred with 5% HOAc in water (50 mL) for 0.5 hours. The organic layer was washed with water (3×50 mL), and stirred with 5% HOAc in water (50 mL) for 2 hours. It was then pumped down to give a sticky material, which was redissolved in chloroform and pumped down again to yield O-EtOCO, N-EtOCO-7,8-dihydronorsinomenine in >80% purity.

Alternatively, 7,8-dihydrosinomenine was dissolved in chloroform. NaHCO$_3$ and MgSO$_4$ were added. The mixture was heated to 62° C. to 66° C. EtOCOCl was slowly added drop-wise to the mixture to form an intermediate compound that was treated with a diluted acid or base to give O-EtOCO, N-EtOCO-7,8 dihydronorsinomenine.

Example 3

Preparation of a Compound Comprising Formula (Ia) Via Step A of Reaction Scheme 1

Sinomenine (3.30 g, 10 mmol) was suspended in CHCl$_3$ (15 mL). NaHCO$_3$ (6 g) was added and the mixture was stirred. Then 3 to 12 equivalents of EtOCOCl were added and the solution incubated at a temperature of 62° C. to 66° C. for between 1 and 7 hours. Water (50 mL) was added and the mixture stirred for 30 minutes to dissolve all of the solids. Chloroform (15 mL) was added and the organic layer was separated and stirred with 5% HOAc in water (2×30 mL). It was then pumped down to give a sticky material, which was re-dissolved in isopropyl acetate and pumped down again to yield O-EtOCO, N-EtOCO-sinomenine in >80% purity.

In another example, sinomenine (3.30 g, 10 mmol) was suspended in chloroform (15 mL), and combined with NaHCO$_3$ (6 g) and MgSO$_4$ (1.5 g). The solution was heated to 62° C. and stirred. Then CH$_3$CHClOCOCl (6×1.1 mL), diluted in CHCl$_3$ to 20 mL, was added drop-wise, with stirring for ~20-30 hours at 62° C. Water (50 mL) was added and the mixture stirred for an hour to dissolve all of the solids. Chloroform was added and the organic layer was separated and stirred in water (3:1, 50 mL) for 1 hour to give CH$_3$CHClOCO—N-sinomenine.

Example 4

Preparation of a Compound Comprising Formula (Ib) Via Step B of Reaction Scheme 1

O-(BzOCO), N-(BzOCO)-7,8-dihydronorsinomenine in isopropyl acetate was stirred at 50° C. under hydrogen (40 psi) overnight to give 7,8-dihydronorsinomenine.

Example 5

Preparation of Compounds Comprising Formula (Ic)

In one example, O-(EtOCO), N-(EtOCO)-7,8,-dihydronorsinomenine was dissolved in chloroform, dried over MgSO$_4$ for 2 hours, and then filtered. CHCl$_3$ (1.0 mL) and 1.0 mL of either (MeSO$_2$)$_2$O, P$_2$O$_5$, POBr$_3$, PBr$_3$, SOBr$_2$, POCl$_3$, or SOCl$_2$ were combined, and added to MeSO$_3$H. The mixture was cooled at room temperature for 30 minutes. The filtered O-EtOCO, N-EtOCO-7,8,-dihydronorsinomenine (0.1 mL) was added and incubated at room temperature for 24 hours. After either 30 minutes or 24 hours at room temperature, or 1 hour at 70° C, 0.1 mL of sample was diluted with 0.033 N NaOH in MeOH/H$_2$O (2:1) and incubated for 10 minutes at a pH of >12. HOAc (0.1 mL) was added and the solution was analyzed by HPLC. Of the control and sample combinations listed in Table 1 below, entries 4, 6, 10, 14, and 16 gave good results of N-(EtOCO)-4,5-epoxy-7,8,-dihydronorsinomenine.

TABLE 1

| Reagent-1 | Reagent-2 | Entries |
|---|---|---|
|  |  | 1 |
|  | MeSO$_3$H | 2 |
| (MeSO$_2$)$_2$O |  | 3 |
| (MeSO$_2$)$_2$O | MeSO$_3$H | 4 |
| P$_2$O$_5$ |  | 5 |
| P$_2$O$_5$ | MeSO$_3$H | 6 |
| POBr$_3$ |  | 7 |
| POBr$_3$ | MeSO$_3$H | 8 |
| PBr$_3$ |  | 9 |
| PBr$_3$ | MeSO$_3$H | 10 |
| SOBr$_2$ |  | 11 |
| SOBr$_2$ | MeSO$_3$H | 12 |
| POCl$_3$ |  | 13 |
| POCl$_3$ | MeSO$_3$H | 14 |
| SOCl$_2$ |  | 15 |
| SOCl$_2$ | MeSO$_3$H | 16 |

In yet another example, dihydrosinomenine (1.6 g) was dissolved in chloroform (80 mL), and cooled to −50° C. MeSO$_3$H (1.7 mL) was added. A solution of Br$_2$ (0.54 mg) in chloroform (10 mL) was added. The mixture was allowed to warm up to 0° C. for 5 minutes. The color became lighter. A solution of 1 N NaOH in water (80 mL) was added to the above reaction mixture. It was stirred at 0° C. for 15 minutes. The organic layer was washed with 1 N NaOH (3×80 mL), and water (2×80 mL). The organic layer was pumped down to dryness to give 3.02 g of solid. Pure product of 4,5-epoxy-dihydrosinomenine can be obtained after chromatography.

Example 6

Preparation of (+)-Norhydromorphone from a Compound Comprising Formula (Ic)

O—ROCO, N—ROCO-dihydronorsinomenine with POCl$_3$ in MeSO$_3$H forms N—ROCO-norhydrocodone. Addition of a proper amount of protic solvent such as water and propionic acid to the above reaction mixture, followed by heating at 100° C., forms (+)-norhydrocodone. Addition of methionine to the reaction mixture followed by heating at 100° C. forms (+)-norhydromorphone.

Example 7

Preparation of (+)-Hydromorphone from a Compound Comprising Formula (Ic)

Treatment of O—ROCO, N—ROCO-7,8-dihydronorsinomenine with BBr$_3$ and HBr sequentially in chloroform forms (+)—N—ROCO-hydrocodone and then (+)-N—ROCO-hydromorphone, which may be further converted to (+)-norhydromorphone after heating in a strong acid solution.

Example 8

Synthesis of (+)-Norhydrocodone (+)-Norhydrocodone was synthesized according to the following scheme:

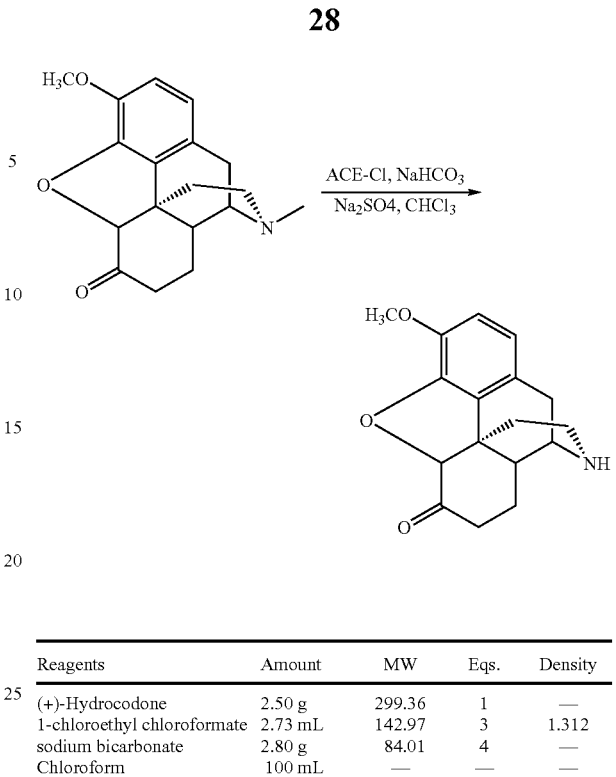

| Reagents | Amount | MW | Eqs. | Density |
|---|---|---|---|---|
| (+)-Hydrocodone | 2.50 g | 299.36 | 1 | — |
| 1-chloroethyl chloroformate | 2.73 mL | 142.97 | 3 | 1.312 |
| sodium bicarbonate | 2.80 g | 84.01 | 4 | — |
| Chloroform | 100 mL | — | — | — |

(+)-Hydrocodone and sodium bicarbonate were suspended in 100 mL of anhydrous chloroform in a 100 mL round bottom flask. The flask was blanketed with nitrogen and heated to reflux. 1-chloroethyl chloroformate was added in four portions. A sample was taken at 2 hr of reflux and analyzed. Another sample was taken from the reaction and evaporated under a stream of nitrogen. It was then quenched by addition of 5% HOAc. Chloroform was added and the aqueous phase was extracted. The chloroform phase was washed one more time with 5% HOAc and then dried over sodium sulfate. The solution was evaporated and the clear oil was analyzed by HPLC.

The reaction was worked up by filtering the solution using a buchner funnel to remove the sodium bicarbonate. The filtrate was evaporated to a beige foam. An attempt to recrystallize the foam from isopropanol or methanol yielded a solid that half oiled out. The solvents were evaporated to a light tan solid. The solid was dried overnight under vacuum to yield 2.58 g. A sample of the solid was analyzed by HPLC.

Example 9

Synthesis of (+)-N-Allyl-Hydrocodone.

(+)—N-allyl-hydrocodone was synthesized according to the following scheme:

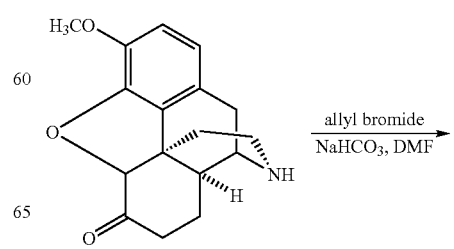

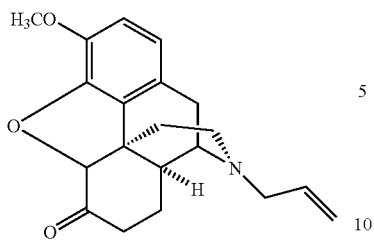

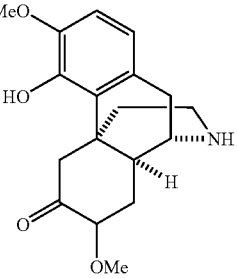

| Reagents | Amount | MW | Eqs. | Density |
|---|---|---|---|---|
| (+)-Norhydrocodone | 6.20 g | 285.34 | 1 | — |
| Allyl Bromide | 3.09 mL | 120.98 | 1.64 | 1.398 |
| Sodium Bicarbonate | 9.16 g | 84.01 | 5.02 | — |
| Dimethylformamide | 125 mL | — | — | — |

(+)-Norhydrocodone was dissolved in dimethylformamide in a 250 mL round bottom flask. The sodium bicarbonate was added. Finally the allyl bromide was added. The flask was blanketed with nitrogen and stirred at room temperature for 3 hr. A sample was taken and analyzed by HPLC. There was still ~30% of the starting material remaining. Another 1.545 mL of allyl bromide and 4.58 g of sodium bicarbonate were added to the reaction. The reaction was allowed to stir overnight at room temperature. Another sample was analyzed by HPLC. No starting material remained in the reaction mixture. The reaction was quenched by adding 100 mL of water. The solution was stirred for 1 hr. The solvents were removed under reduced pressure. The residue was resuspended between DCM and water. The aqueous layer was extracted 2× with DCM. The combined organic extracts were washed with saturated NaHCO$_3$ and 20% NaCl. The organic layer was dried over sodium sulfate and evaporated to dryness. The resulting brown oil was dried overnight under vacuum. A sample was analyzed by HPLC. The oil yielded 6.00 g (85%).

Example 10

Synthesis of Nordihydrosinomenine

Nordihydrosinomenine was synthesized according to the following scheme:

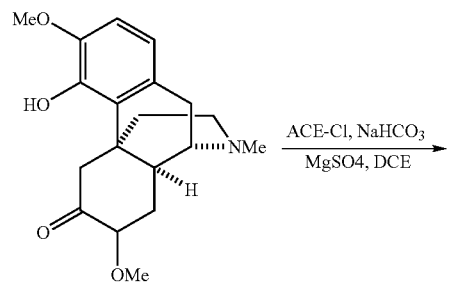

Dihydrosinomenine (10.0 g, 30.3 mmol) was dissolved in 150 mL of 1,2-dichloroethane under a blanket of nitrogen. To this solution was added sodium bicarbonate (7.6 g, 90.5 mmol) and anhydrous MgSO$_4$ (14.5 g, 120.7 mmol). The resulting suspension was then heated to 65° C., and 1-chloroethylchoroformate (25.0 g, 175 mmol) was carefully added drop-wise over a period of 10 minutes. Upon completion of the addition, the progress of the reaction was monitored by HPLC. After 1.5 hours, the reaction was complete and allowed to cool to room temperature. The suspension was then filtered to remove the solids and quenched with an equal volume of a 1% solution of formic acid in water. The resulting biphasic mixture was stirred vigorously overnight at room temperature. The pH of the solution was then increased to pH 10 with conc. ammonium hydroxide. The phases were separated, and the aqueous phase was extracted once more with dichloroethane. The combined organic phases were dried over MgSO$_4$, filtered, and evaporated to give the product as a light-brown foam (2.8 g).

Example 11

Synthesis of N-Cyclopropylmethyl-Dihydrosinomenine

N-cyclopropylmethyl-dihydrosinomenine was prepared according to the following scheme:

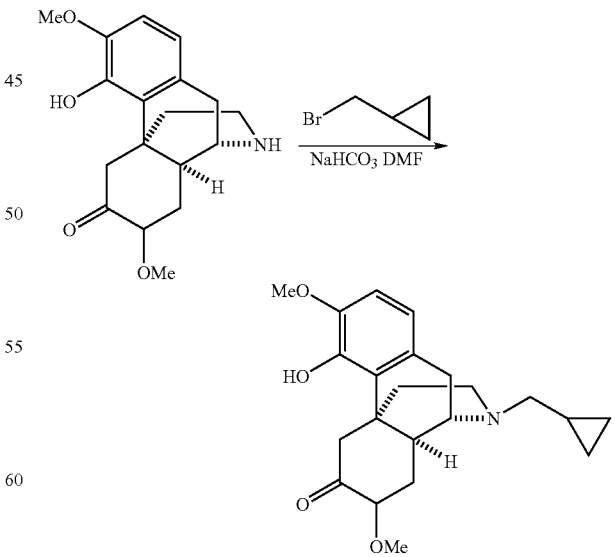

Nordihydrosinomenine (1.73 g, 5.5 mmol) was dissolved in anhydrous DMF (8.0 mL) under an nitrogen atmosphere. To this solution was added NaHCO$_3$ (0.92 g, 10.9 mmol) and cyclopropylmethyl bromide (688 µL, 7.1 mmol). The resulting solution was stirred at 50° C. for 65 h. HPLC analysis revealed that the reaction was complete, so the reaction was quenched by the addition of 20 mL H₂O. The resulting solution was then extracted with dichloromethane (3×30 mL), and the combined organic phases were evaporated to a give a brownish oil. To remove most of the residual DMF, the oil was treated with n-heptane (100 mL) and stripped on the rotary evaporator under high vacuum. This was repeated four times until a brown foam was obtained. The crude product was then subjected to purification by flash chromatography on silica gel (2:1, Chloroform:CMA; CMA=90:9:1, Chloroform:Methanol:Ammonium hydroxide). The combined fractions were evaporated to give the product as an off-white solid (0.546 g). m/z=372. 30 (M+H); $^1$H NMR and $^{13}$C NMR were consistent with the desired product. 2D-COESY NMR showed an absence of correlation between H-7 and H-14, suggesting that the stereochemistry was S at position 7.

Example 12

Synthesis of N-Allyl-Dihydrosinomenine

N-allyl-eihydrosinomenine was prepared according to the following scheme:

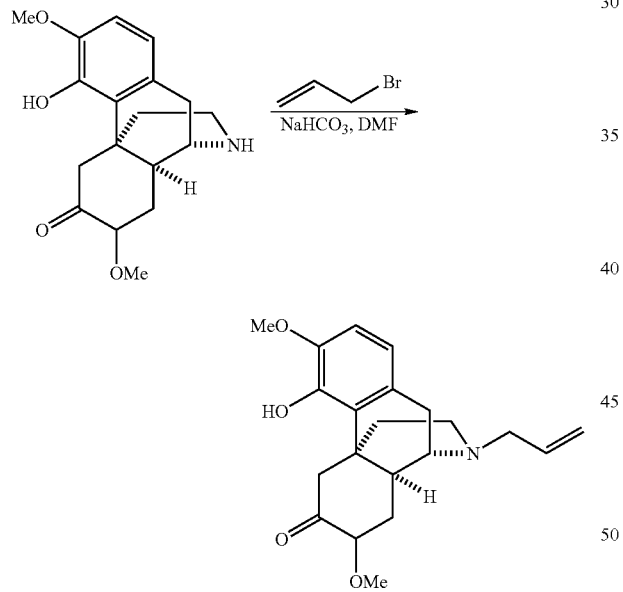

Nordihydrosinomenine (50 mg, 0.16 mmol) was dissolved in 5 mL anhydrous DMF under a nitrogen atmosphere. Sodium carbonate (27 mg) was then added, and the reaction was allowed to stir at room temperature for 10 minutes. Allyl bromide (17 µL, 0.2 mmol) was then added, and the progress of the reaction was monitored by HPLC. After 16 hr, the reaction was quenched with 10 mL H₂O, and the resulting solution was extracted with dichloromethane (3×15 mL). The combined organic phases were evaporated to a give a brownish oil. The crude product was purified by preparative reversed-phase chromatography to give the product as an off-white solid. MS: M+H⁺=358.22.

Reaction Scheme for the Synthesis of Compounds 2, 3, and 4.

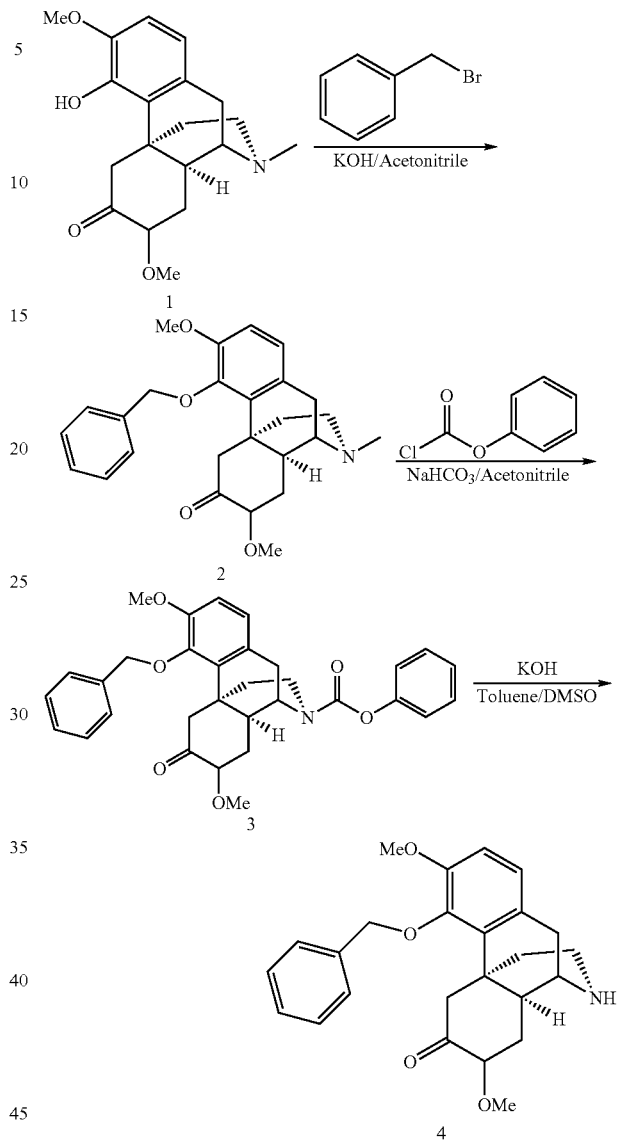

Example 13

Synthesis of 4-Benzyl-Dihydrosinomenine
(Compound 2)

To a mixture of dihydrosinomenine (10 g, 0.0302 mole, one eq.) in acetonitrile (200 mL) was added powdered KOH (6 g, 0.111 mole, 3.68 eq.); the resulting mixture was stirred at room temperature for about 30 min and then benzyl bromide (3.8 mL, 0.0317 mole, 1.05 eq.) was added. The reaction gradually turned from pink to colorless, and plenty of white precipitates were formed. After stirring for 15 min, 200 mL water was added, the product was extracted with dichloromethane (3×150 mL); the combined organic phase was washed with water (3×150 mL) and dried over anhydrous magnesium sulfate. After removing the dried organic phases, the there was 13 g of light yellow solid, with a purity of 83%.

Example 14

Synthesis of 4-Benzyl-N-Phenoxycarbonyidihydrosinomenine (Compound 3)

To the cooled mixture of 4-benzyl-dihydrosinomenine (10 g, 0.024 mole, one eq.), sodium bicarbonate (12 g, 0.0653 mole, three eq.) and acetonitile (65 mL) were added. The reaction flask was placed in an ice bath and phenylchloroformate (12.9 mL, 0.103 mole, 4.3 eq.) was added drop-wise. The resulting mixture was gradually heated to 63° C. (oil bath temperature) for six hours. After cooling to room temperature, 350 mL ethyl acetate was added to the reaction mixture, followed by addition of 200 mL water. The organic phase was separated; the aqueous phase was extracted with ethyl acetate (2×100 mL); the combined organic phases were washed with 3N NaOH aqueous solution (5×150 mL), water (200 mL), and dried over anhydrous magnesium sulfate. After filtering the drying reagents, the filtrate was evaporated to remove volatiles. The residue was further purified on silica gel chromatography with 1:1 EtOAc/heptane, and gave 3.3 g of product with a purity of 95%. LC-MS: M+1=528.13

Example 15

Synthesis of 4-Benyzl-Nordihydrosinominene (Compound 4)

A mixture of 4-benzyl-N-phenoxycarbonyl-dihydrosinomenine (1.0 g, 1.9 mmole, one eq.), dimethyl sulfoxide (1 mL), toluene (4 mL), and potassium hydroxide (0.5 g, 8.7 mmole, 4.7 eq.) was heated to 86° C. (oil bath) for four hrs. After the reaction was cooled to room temperature, 100 mL ethyl acetate was added to the reaction. The resulting mixture was washed with 2N NaOH (5×50 mL) and water (50 mL). The organic phase was dried over anhydrous magnesium sulfate. After removing the volatiles, it gave 0.6 g brown oil. The crude material was purified on silica gel chromatography with a mixture of EtOAc/DCM/MeOH+1% Et₃N; it gave 0.2 g of sticky light brown oil with a purity of 92%. LC-MS: M+1=408.21.

What is claimed is:

1. A compound having a formula (Ia):

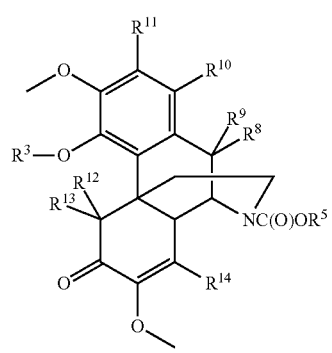

(Ia)

wherein:
$R^3$ is selected from the group consisting of hydrogen, {-}C(O)$R^6$, and {-}$R^6$;
$R^5$ is selected from the group consisting of alkyl having from 1 to 8 carbons, CH$_3$CHCl—{-} and CH$_2$=CH—{-};
$R^6$ is selected from the group consisting of hydrocarbyl and hydrocarbyl substituted with at least one atom other than carbon;
$R^8$ and $R^9$ are independently selected from the group consisting of hydrogen, hydroxyl, hydrocarbyl, and hydrocarbyl substituted with at least one atom other than carbon, or $R^8$ and $R^9$ together form a carbonyl group;
$R^{12}$ and $R^{13}$ are independently selected from the group consisting of hydrogen, hydrocarbyl, and hydrocarbyl substituted with at least one atom other than carbon, or $R^{12}$ and $R^{13}$ together form a carbonyl group; and
$R^{10}$, $R^{11}$, and $R^{14}$ are independently selected from the group consisting of hydrogen, hydrocarbyl, hydrocarbyl substituted with at least one atom other than carbon, and a halogen.

2. A compound having a formula (Ib):

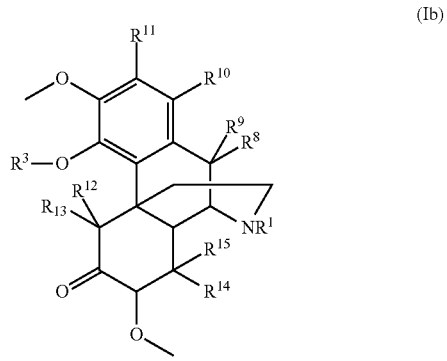

(Ib)

wherein:
$R^1$ is selected from the group consisting of hydrogen, and {-}C(O)$R^5$;
$R^3$ is selected from the group consisting of hydrogen, {-}C(O)$R^6$, and {-}$R^6$;
$R^5$ and $R^5$ are independently selected from the group consisting of hydrocarbyl and hydrocarbyl substituted with at least one atom other than carbon;
$R^8$ and $R^9$ are independently selected from the group consisting of hydrogen, hydroxyl, hydrocarbyl, and hydrocarbyl substituted with at least one atom other than carbon, or $R^8$ and $R^9$ together form a carbonyl group;
$R^{12}$ and $R^{13}$ are independently selected from the group consisting of hydrogen, hydrocarbyl, and hydrocarbyl substituted with at least one atom other than carbon, or $R^{12}$ and $R^{13}$ together form a carbonyl group; and
$R^{10}$, $R^{11}$, $R^{14}$ and $R^{15}$ are independently selected from the group consisting of hydrogen, hydrocarbyl, hydrocarbyl substituted with at least one atom other than carbon, and a halogen, or $R^{14}$ and $R^{15}$ together form a carbonyl group.

3. A process for the preparation of compound (Ib) according to the following reaction scheme:

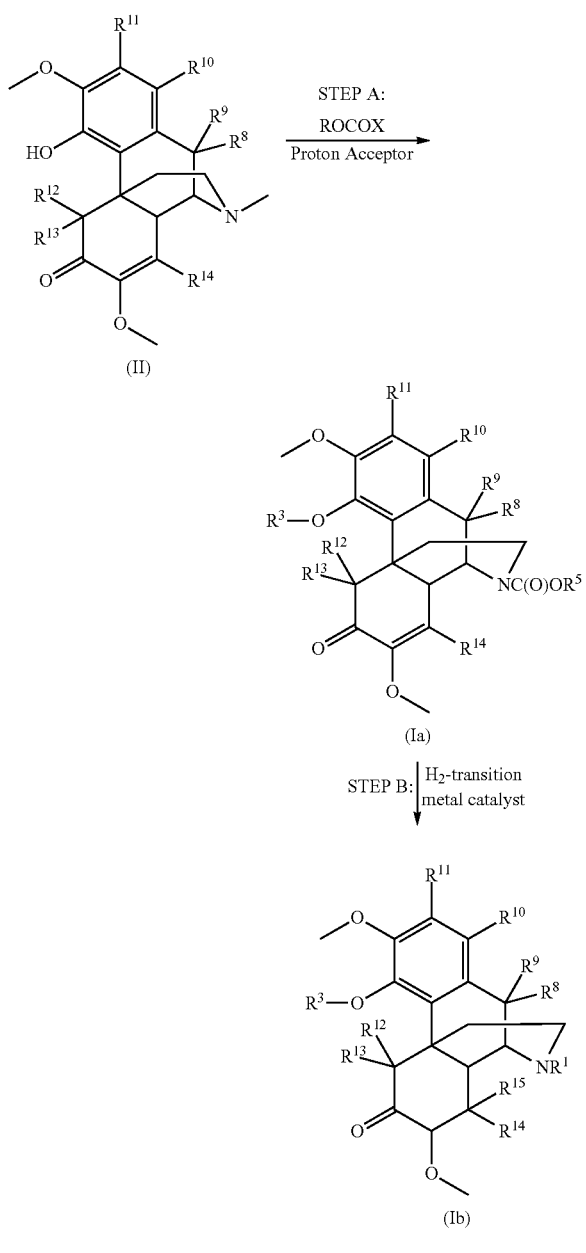

(II)

(Ia)

STEP B: H₂-transition metal catalyst (Ib)

wherein:
R is selected from hydrocarbyl, and hydrocarbyl substituted with at least one atom other than carbon;
R¹ is selected from the group consisting of hydrogen and {−}C(O)R⁵;
R³ is selected from the group consisting of hydrogen, {−}C(O)R⁶, and {−}R⁶;
R⁵ and R⁶ are independently selected from the group consisting of hydrocarbyl and hydrocarbyl substituted with at least one atom other than carbon;
R⁸ and R⁹ are independently selected from the group consisting of hydrogen, hydroxyl, hydrocarbyl, and hydrocarbyl substituted with at least one atom other than carbon, or R⁸ and R⁹ together form a carbonyl group;
R¹², and R¹³ are independently selected from the group consisting of hydrogen, hydrocarbyl, and hydrocarbyl substituted with at least one atom other than carbon, or R¹² and R¹³ together form a carbonyl group;

R¹⁰, R¹¹, and R¹⁴ are independently selected from the group consisting of hydrogen, hydrocarbyl, hydrocarbyl substituted with at least one atom other than carbon, and a halogen;

R¹⁵ is hydrogen; and

X is a halogen.

4. The process of claim 3, wherein R, R⁵ and R⁶ are independently selected from the group consisting of an alkyl group having from 1 to 8 carbon atoms, an aryl group, CH₃CHCl—{−}, and an {−}CH₂-aryl group, and X is chlorine.

5. The process of claim 3, the molar ratio of the compound comprising formula (II) to ROCOX to proton acceptor is from about 1:3:1 to about 1:12:12; the proton acceptor is a salt with a pH greater than 7; the reaction of Step A is conducted in the presence of an aprotic solvent; and at a temperature ranging from about 45° C. to about 120° C.; the molar ratio of compound (Ia) to transition metal catalyst is from about 1:0.0005 to about 1:0.005, the reaction of Step B is conducted under pressurized hydrogen having a pressure from about 0 to about 500 PSI, the reaction of Step B is conducted in the presence of a methanol-containing solvent, and at a temperature ranging from about 20° C. to about 120° C.

6. A process for the preparation of compound (Ib) according to the following reaction scheme:

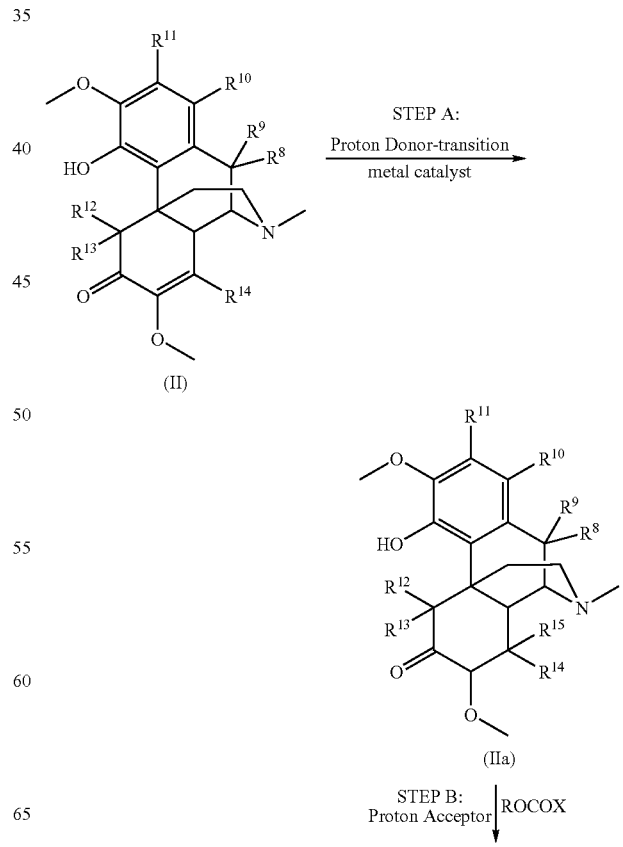

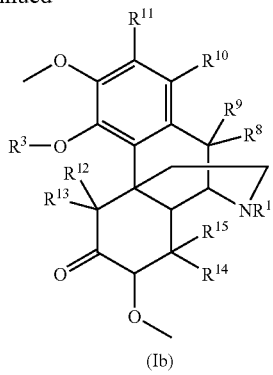

(Ib)

wherein:

R is selected from hydrocarbyl, and hydrocarbyl substituted with at least one atom other than carbon;

$R^1$ is selected from the group consisting of hydrogen and $\{-\}C(O)R^5$;

$R^3$ is selected from the group consisting of hydrogen, $\{-\}C(O)R^6$, and $\{-\}R^6$;

$R^5$ and $R^6$ are independently selected from the group consisting of hydrocarbyl and hydrocarbyl substituted with at least one atom other than carbon;

$R^8$ and $R^9$ are independently selected from the group consisting of hydrogen, hydroxyl, hydrocarbyl, and hydrocarbyl substituted with at least one atom other than carbon, or $R^8$ and $R^9$ together form a carbonyl group;

$R^{12}$, and $R^{13}$ are independently selected from the group consisting of hydrogen, hydrocarbyl, and hydrocarbyl substituted with at least one atom other than carbon, or $R^{12}$ and $R^{13}$ together form a carbonyl group;

$R^{10}$, $R^{11}$, and $R^{14}$ are independently selected from the group consisting of hydrogen, hydrocarbyl, hydrocarbyl substituted with at least one atom other than carbon, and a halogen;

$R^{15}$ is hydrogen; and

X is a halogen.

7. The process of claim 6, wherein R, $R^5$ and $R^6$ are independently selected from the group consisting of an alkyl group having from 1 to 8 carbon atoms, an aryl group, $CH_3CHCl-\{-\}$, $CH_2=CH-\{-\}$, and an $\{-\}CH_2$-aryl group, and X is chlorine.

8. The process of claim 6, wherein the molar ratio of the compound comprising formula (II) to proton donor to transition metal catalyst is from about 1:0.5:0.0005 to about 1:10:0.05, the of reaction of Step A is conducted under pressurized hydrogen having a pressure from about 0 to about 500 PSI, the reaction of Step A is conducted in the presence of a methanol-containing solvent, and the at a temperature ranging from about 20° C. to about 120° C.; the molar ratio of the compound comprising formula (IIa) to ROCOX to proton acceptor is from about 1:2:1 to about 1:20:20, the reaction of Step B is conducted in the presence of an aprotic solvent, and at a temperature ranging from about 45° C. to about 120° C.

9. The process of claim 8, wherein the proton donor is selected from the group consisting of HOAc, $HCO_2H$, HCl, and $H_2SO_4$; the transition metal catalyst is selected from the group consisting of Pd/C, Pt/C, Ru/C, and Rh/C; and the proton acceptor is selected from the group consisting of $NaHCO_3$, $KHCO_3$, $LiHCO_3$, $Na_2CO_3$, $K_2CO_3$, $Li_2CO_3$, and combinations thereof.

* * * * *